United States Patent
Horne et al.

(10) Patent No.: US 6,197,954 B1
(45) Date of Patent: *Mar. 6, 2001

(54) INTERMEDIATES FOR THE SYNTHESIS OF DEBROMOHYMENIALDISINE AND PROCESSES THEREOF

(75) Inventors: David A. Horne; Kenichi Yakushijin, both of New York, NY (US)

(73) Assignee: The Trustees of Columbia University in the City of New York, New York, NY (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/016,748

(22) Filed: Jan. 30, 1998

(51) Int. Cl.$^7$ .................. C07D 487/04; C07D 521/00

(52) U.S. Cl. ............................................. 540/521

(58) Field of Search .............................. 540/521

(56) References Cited

U.S. PATENT DOCUMENTS

| | | | |
|---|---|---|---|
| 3,746,705 | 7/1973 | Cavalleri et al. | 260/240 |
| 4,812,462 | 3/1989 | Blankley et al. | 514/303 |
| 5,091,390 | 2/1992 | Ardecky et al. | 514/303 |
| 5,621,099 | 4/1997 | Annoura et al. | 540/521 |
| 5,834,609 | * 11/1998 | Horne et al. | 540/476 |

FOREIGN PATENT DOCUMENTS

| | | |
|---|---|---|
| 2016437 | 11/1990 | (CA) . |
| WO8707274 | 12/1987 | (WO) . |

OTHER PUBLICATIONS

Kobayashi et al., Experimentia (1988), 42(9), 1064–1065, 1986.*

Braun, M., et al., Journal of the American Chemical Society (1978), "Synthesis of Parazoanthoxanthins and Pseudozoanthoxanthins," vol. 100, pp. 4208–4213; U.S.A. .

Braun, M., et al., Journal of the American Chemical Society (1976), "The Synthesis of Zoanthoxanthins," vol. 32, pp. 3049–3050; U.S.A. .

Colson, Genevieve et al., "Mode of Action of the Antitumor Compound Girodazole", Chemical Abstracts 117:82994y, (1992).

Commercon, A., et al., Tetrahedron Letters (1991), "A Diastereoselective Synthesis of Girolline," vol. 32, pp. 1419–1422; U.K. .

Dalkafouki, A., et al., Tetrahedron Letters (1991), "Synthesis of 2–Dimethylaminoimidazole Derivatives: A New Access to Indolyl–imidazole Alkaloids of Marine Origina," vol. 32 pp. 5325–5328; U.K. .

Fernandez–Bolanos, J., et al., "Synthesis of 1–Alkyl (or H)–4–(D–lyxo–tetritol–1–yl)–4–imidazolin–2–ylideneammonium Picrates and Chlorides", Chemical Abstracts 116: 255934p, (1992).

Grimmett, M.R., "imidazoles and their Benzo Derivatives: (ii) Reactivity," in Comprehensive Heterocyclic Chemistry: The Structure, Reactions, Synthsis and Uses of Heterocyclic Compounds, Potts, K.T., et.; Pergamon Press, New York (1984), vol. 5, pp. 404–405; U.S.A. .

Kobayaski, J., et al., "α–Adrenoceptor blocking action of hymenin, a novel marine alkaloid", Chemical Abstracts, 108(15): 124371q (1988).

Lancini, G., et al., United Kingdom patent 1,132,013, "Imidazole Derivatives," published Oct. 30, 1968.

Lancini, G., et al., Journal of Heterocyclic Chemistry (1966), "A New Synthesis of Alkyl and Aryl 2–Amino–imidazoles," vol. 3, pp. 152–154; U.S.A. .

Ruccia, M., et al, Tetrahedron (1974), "Mononuclear Heterocyclic Rearrangements–VI: Conversion of 1,2,4–Oxadiazoles into Imidazoles," vol. 30, pp. 3859–3864; U.K. .

Walker, R., et al, Journal of the American Chemical Society (1981), "Sceptrin, an Antimicrobial Agent from the sponge Agelas Sceptrum," vol. 103, pp. 6772–6773; U.S.A. .

Xu, Y., et al., "Reactions of 2–Aminoimidazoles with Aldehydes. Hydroxyalkylation and Cycloaddition", Tetrahedron Letters (1993), 34(44):6981–6984.

Zurita, M., et al., Tetrahedron Letters (1991), "A Diastereoselective Synthesis of Girolline," vol. 45, pp. 6713–6720; U.K. .

Supriyono, A. et al. (1995) "Bioactive Alkaloids from the Tropical Marine Sponge *Axinella carteri*, ", Naturforsch 50:669–674.

* cited by examiner

*Primary Examiner*—Mukund J. Shah
*Assistant Examiner*—Bruck Kifle
(74) *Attorney, Agent, or Firm*—John P. White; Cooper & Dunham LLP

(57) ABSTRACT

The synthesis of $C_{11}N_5$ marine sponge alkaloids (±)-hymenin (1), stevensine (2), hymenialdisine (3), and debromohymenialdisine (4) is described. These natural products are the primary family members of the sponge metabolites that contain a fused pyrrolo[2,3-c]azepin-8-one ring system with either a 2-aminoimidazole (AI) or glycocyamidine appendage. The key steps in the synthesis centered around the generation of novel azafulvenium ions and their regioselective heterodimerization with AI in order to create the tricyclic core. A rarely used protodebromination/oxidation strategy was employed to selectively generate the desired a-bromo substitution pattern seen in hymenialdisine (3). In addition, the AI moiety was shown to be a useful precursor to the glycocyamidine unit found in 3 and 4, which suggests that AI derived natural products may be the biogenic forerunners to glycocyamidine metabolites.

21 Claims, 10 Drawing Sheets

Hymenin (1)

Stevensine (2)

Hymenialdisine (3) R=Br

Debromohymenialdisine (4) R=H

AI

R=H or Br
A

Scheme 2[a]

[a] Key: (a) Br$_2$, MeOH, 20 min, RT, 95%; (b) TFA, RT, 3 d, 50%; (c) CH$_3$SO$_3$H, RT, 46% (19), 20% (17); (d) CH$_3$SO$_3$H, RT, 96%.

Scheme 3[a]

[a] Key: (a) CH$_3$SO$_3$H, 90 °C, sealed tube, 14% (20), 47% (21); (b) CH$_3$SO$_3$H, 90 °C, unsealed, 61%.

Scheme 4[a]

[a] Key: (a) Br$_2$, TFA, RT, 95%; (b) Br$_2$, CH$_3$SO$_3$H, RT, 21% (22), 38% (23); (c) ref. 19.

Scheme 5[a]

[a] Key: (a) HBr (aq), 90 °C, sealed tube, 21% (24), 40% (4); (b) HOAc/H$_2$O, reflux, 72%; (c) CH$_3$SO$_3$H, HBr (cat.), 90 °C, sealed tube, 12 h, 33% (3), 27% (4); (d) same as (b), 2 d, 65%.

Scheme 6

INTERMEDIATES FOR THE SYNTHESIS OF DEBROMOHYMENIALDISINE AND PROCESSES THEREOF

The invention disclosed herein was made with U.S. Government support from the National Institutes of Health (R01-GM50929). Accordingly, the U.S. Government has certain rights in this invention.

Throughout this application, various references are referred to by superscripted numbers. Disclosures of these publications in their entireties are hereby incorporated by reference into this application to more fully describe the state of the art to which this invention pertains. Full bibliographic citation for these references may be found at the end of this application, preceding the claims, in numerical order corresponding to the superscripted numbers.

BACKGROUND OF THE INVENTION

A number of structurally unique $C_{11}N_5$ marine metabolites containing guanidine and either brominated or nonbrominated pyrrole moieties have been isolated from various sponges.[1] Among these are the tricyclic natural products hymenin (1),[2] stevensine (2),[3,4] hymenialdisine (3),[4–8] and debromohymenialdisine (4).[4–9] This group of natural products share in common a fused bicyclic pyrrolo[2,3-c]azepin-8-one ring system that bears either a 2-aminoimidazole (AI) or glycocyamidine appendage. Their structures were elucidated primarily from spectral studies in comparison with biogenetically and structurally related sponge metabolites. The X-ray crystal structure of 3 has been reported by two research groups.[5,6] Hymenialdisine (3) is the only metabolite among the $C_{11}N_5$ and dimerically related natural products that contains a monobromo pyrrole moiety in which the bromine atom is situated in the a position.[10] This invention describes a synthesis of this family of natural products consisting of 1–4.

SUMMARY OF THE INVENTION

The present invention provides a process for producing hymenialdisine and debromohymenialdisine from hymenin via several different pathways for their synthesis.

The present invention further provides the novel compounds which are more fully described and depicted in the Detailed Description, Experimental Details, Claims and Figures. These novel compounds are intermediates or by products of the above pathways. As these compounds are produced in the synthesis of hymenialdisine and debromohymenialdisine, the process for producing these novel compounds is also provided by this invention.

DETAILED DESCRIPTION

Figure 1:
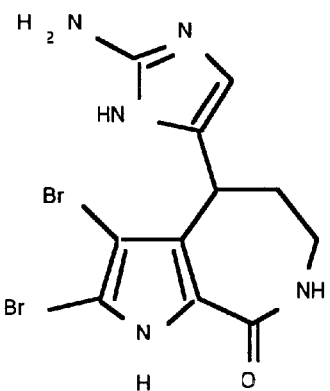
FIG. 1 Schematic depiction of the compounds hymenin (1), stevensine (2), hymenialdisine (3), and debromohymenialdisine (4).
Figure 1:
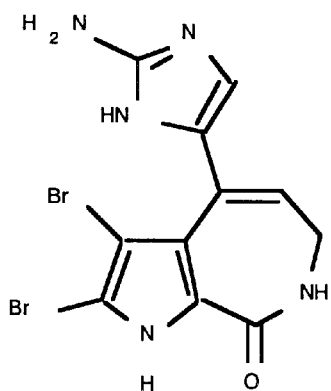
Figure 1:
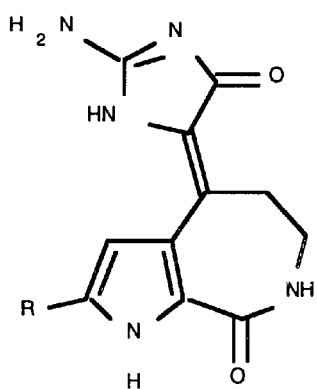
Figure 2:
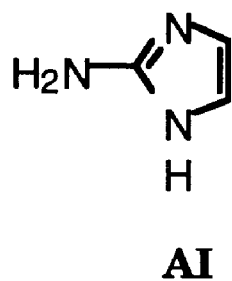
FIG. 2 Schematic depiction of 2-aminoimidazole (AI) and azafulvene (A).
Figure 2:
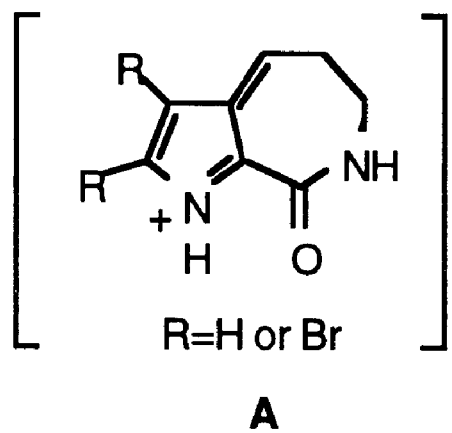
Figure 3:
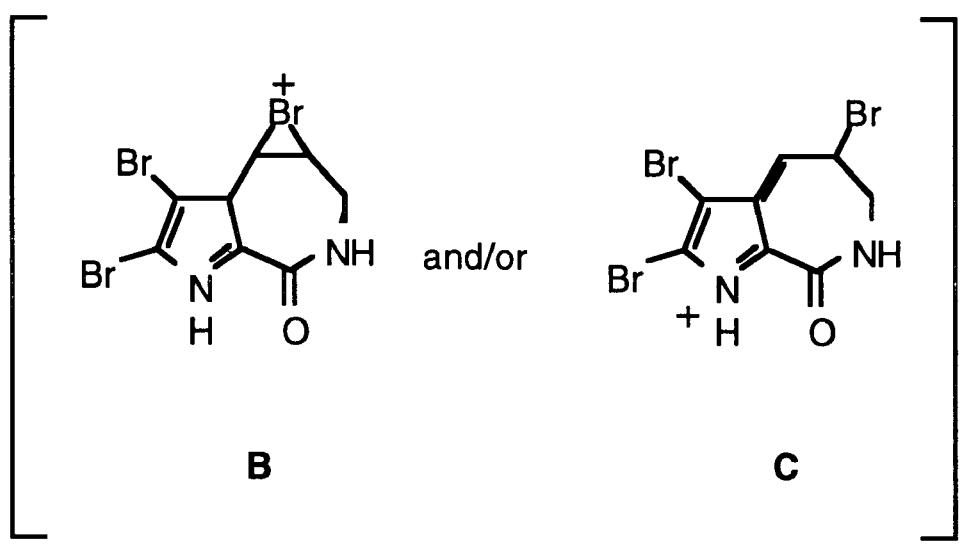
FIG. 3 Schematic depiction of the bridged bromonium ion (B) and the azafulvenium ion (C).
Figure 4:
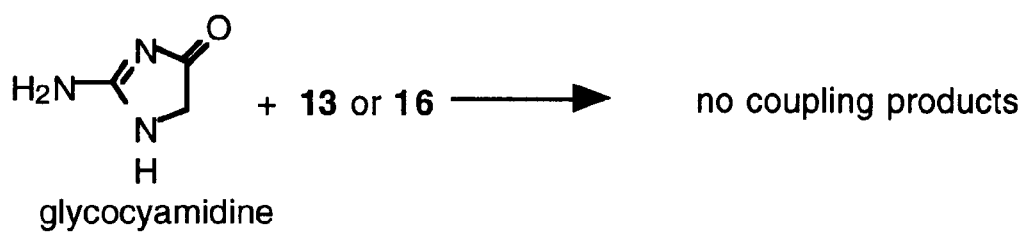
FIG. 4 Schematic depiction of a reaction between glycocyamidine and olefins (13) and (16).
Figure 5:
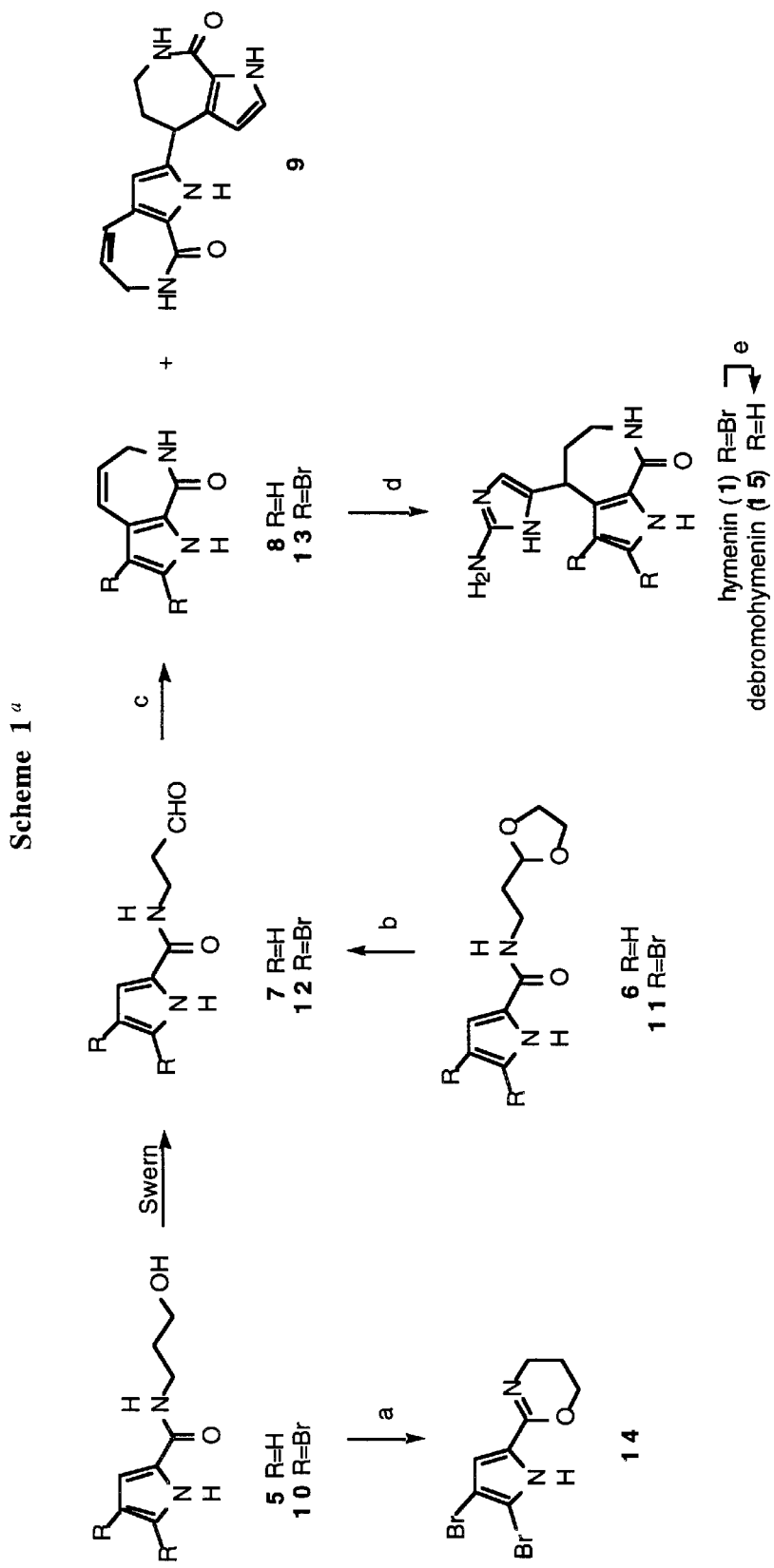
FIG. 5 Scheme 1. Schematic depiction of reactions in the synthesis of hymenin (1).
Figure 6:
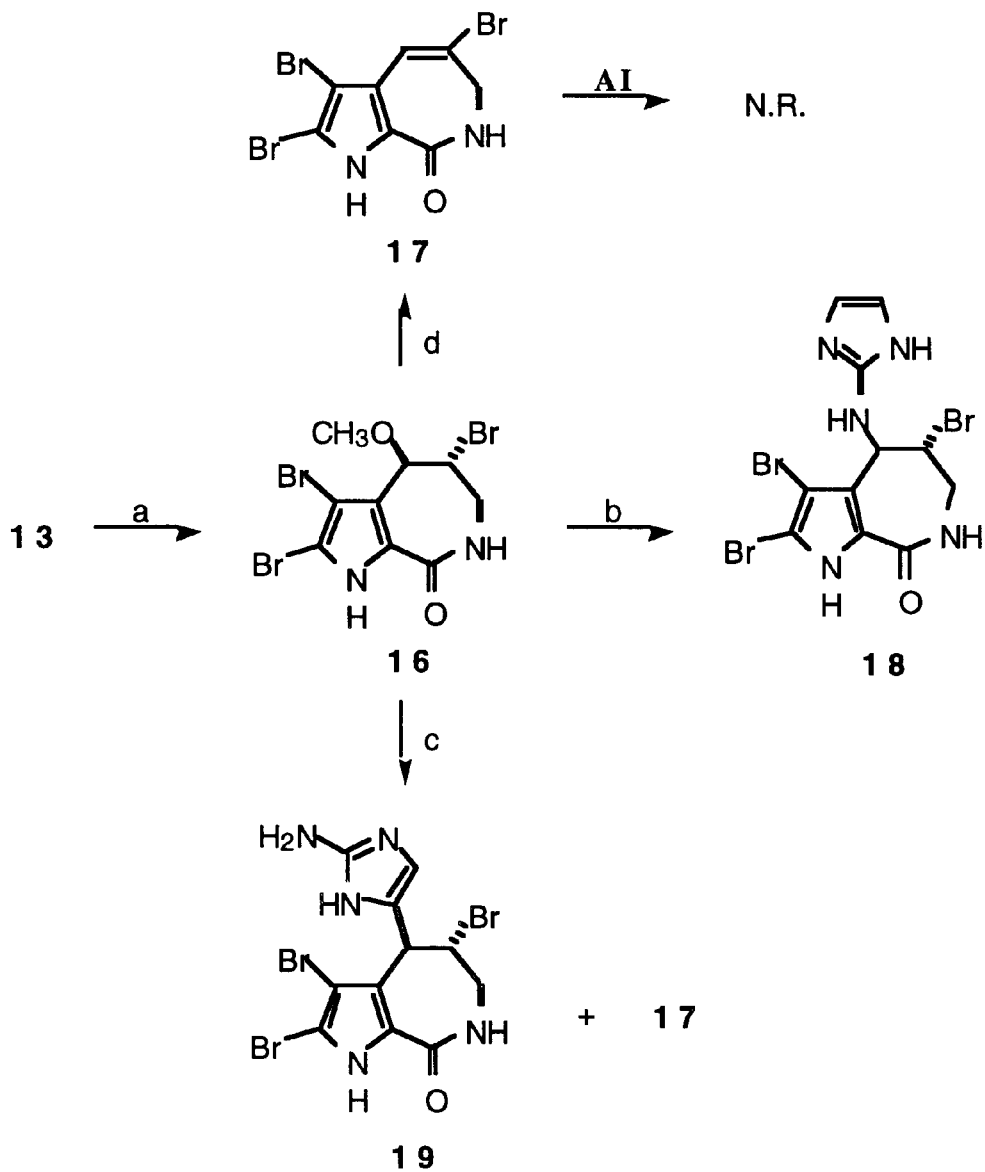
FIG. 6 Scheme 2. Schematic depiction of reactions in the synthesis of stevensine (2).
Figure 7:
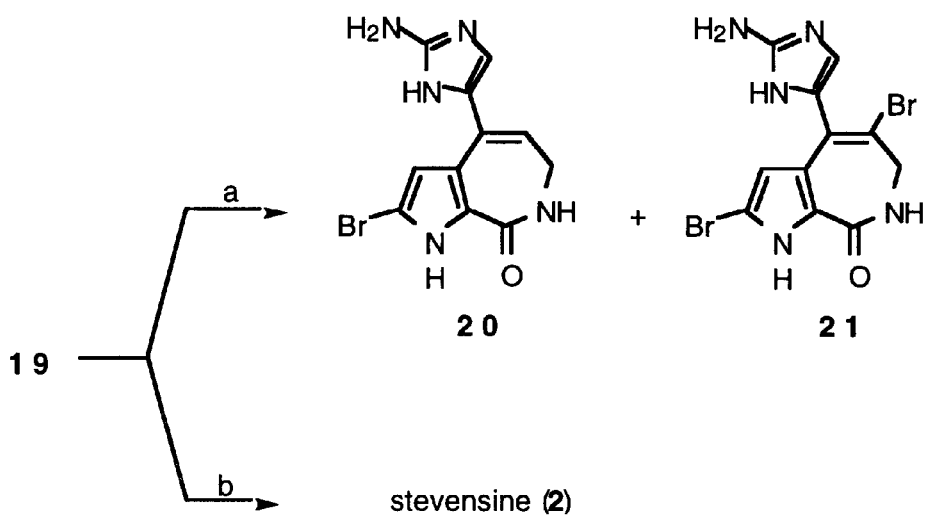
FIG. 7 Scheme 3. Schematic depiction of reactions in the synthesis of stevensine (2).
Figure 8:
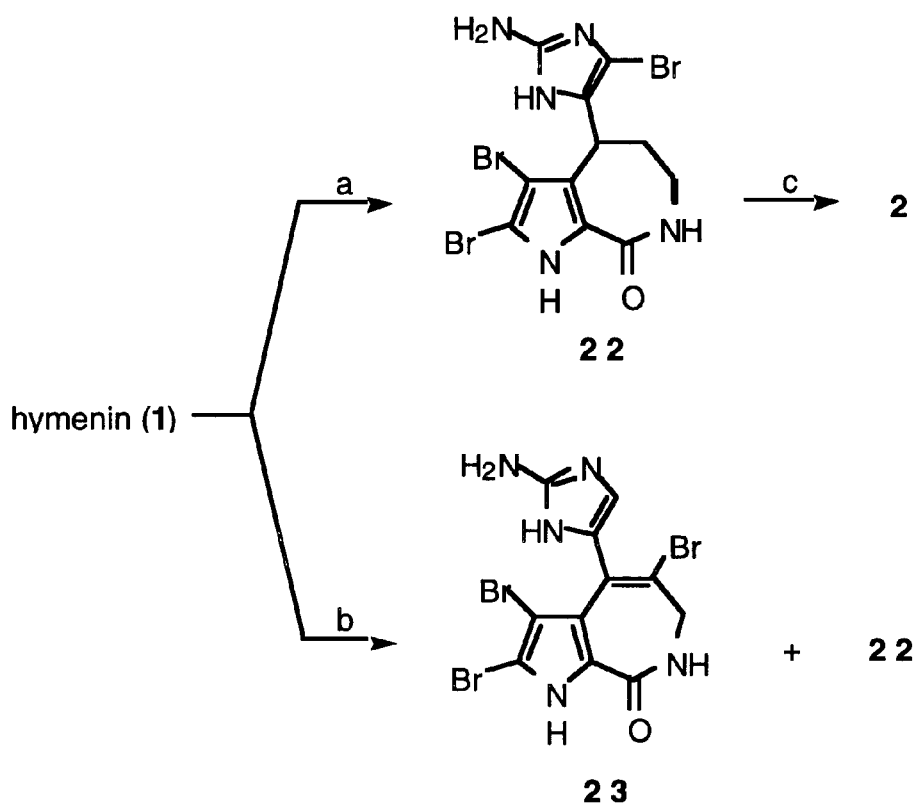
FIG. 8 Scheme 4. Schematic depiction of reactions in the synthesis of hymenialdisine (3) and debromohymenialdisine (4).
Figure 9:
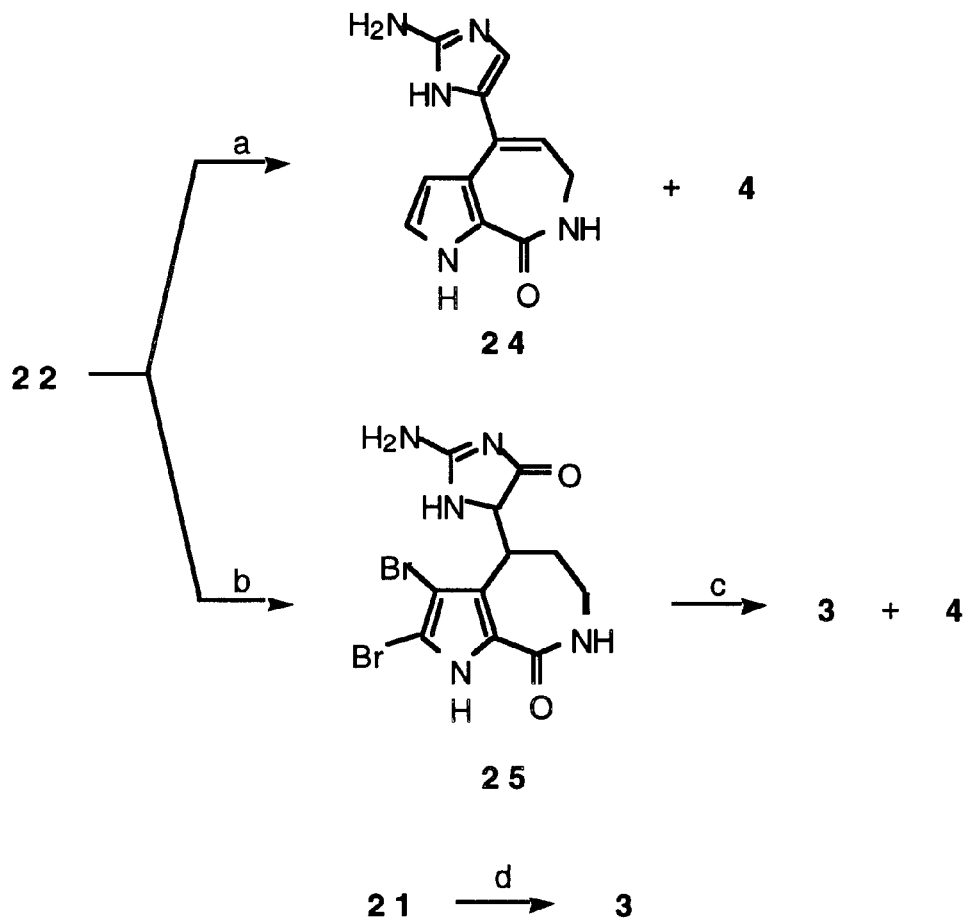
FIG. 9 Scheme 5. Schematic depiction of reactions in the synthesis of hymenialdisine (3) and debromohymenialdisine (4).
Figure 10:
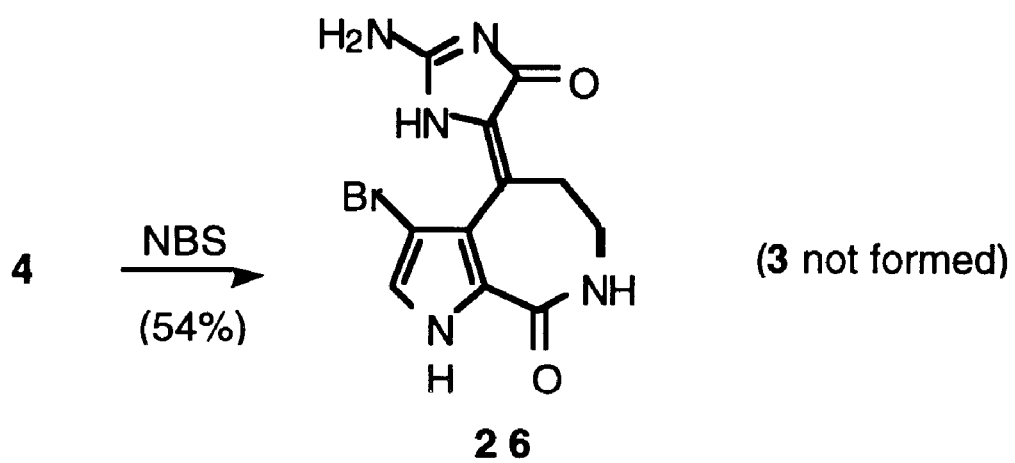
FIG. 10 Scheme 6. Schematic depiction of a reaction between debromohymenialdisine and N-bromosuccinamide to produce 3-bromodebromohymendialdisine.

The present invention provides a compound having the structure:

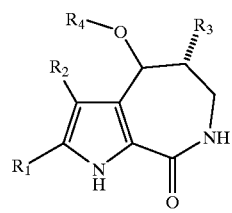

where $R_1$ and $R_2$ are the same or different and are H or a halogen, $R_3$ is a hydroxy group or a halogen and $R_4$ is an alkyl, a methyl or an acyl group.

In a further embodiment, $R_1$, $R_2$, and $R_3$ are Br and $R_4$ is a methyl group.

The present invention also provides a compound having the structure:

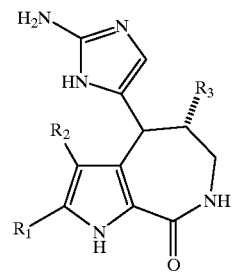

wherein $R_1$ and $R_2$ are the same or different and are H or a halogen and $R_3$ is a hydroxy group or a halogen. In a further embodiment, $R_1$, $R_2$, and $R_3$ are Br.

The present invention provides compound having the structure:

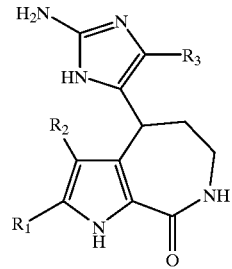

where $R_1$ and $R_2$ are the same or different and are H or a halogen and $R_3$ is a halogen. In a further preferred embodiment, $R_1$, $R_2$, and $R_3$ are Br.

The present invention provides a compound having the structure:

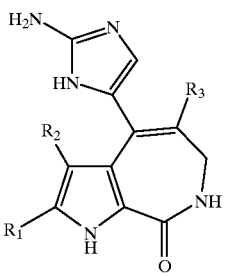

where $R_1$, $R_2$, and $R_3$ are the same or different and are H or a halogen. In a specific embodiment, $R_1$ and $R_3$ are Br and $R_2$ is H. In another embodiment, $R_1$, $R_2$, and $R_3$ are Br. In a further embodiment, $R_1$, $R_2$, and $R_3$ are H.

This invention also provides a compound having the structure:

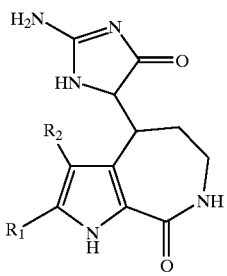

where $R_1$ and $R_2$ are the same or different and are H or a halogen. In an embodiment, $R_1$ and $R_2$ are Br.

The present invention provides a compound having the structure:

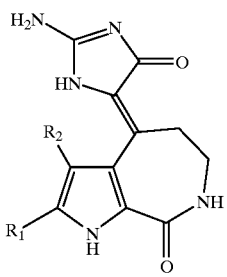

where $R_1$ and $R_2$ are the same or different and are H or a halogen except when $R_2$ is H then $R_1$ is not H or Br. In an embodiment, $R_1$ is H and $R_2$ is Br.

This invention also provides a process for producing debromohymenialdisine, by reacting a first compound with the structure

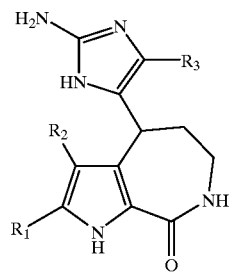

with aqueous HBr at about 90° C. in a sealed tube. In an embodiment, $R_1$, $R_2$, and $R_3$ are Br.

In a further embodiment, the first compound is produced by a second process reacting a second compound with the structure:

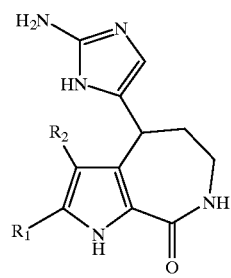

with a halogenating agent and trifluoroacetic acid at about room temperature.

In another embodiment, the first compound is produced by a second process comprising reacting a second compound with the structure:

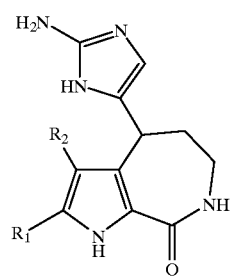

with a halogenating agent and $CH_3SO_3H$ at about room temperature. In an embodiment, $R_1$ and $R_2$ are Br.

In another embodiment, the second compound is produced with $Br_2$ and trifluoroacetic acid at about room temperature.

In an embodiment, the second compound is produced with $Br_2$ and $CH_3SO_3H$ at about room temperature.

This invention further provides a second process for producing debromohymenialdisine, by reacting a first compound with the structure:

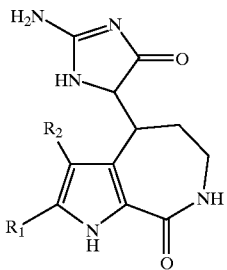

with CH$_3$SO$_3$H and catalytic HBr at about 90° C. in a sealed tube for about 12 hours. In an embodiment, R$_1$ and R$_2$ are Br.

In a further embodiment, the first compound is produced by reacting a second compound with the structure

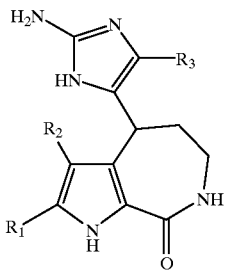

with acetic acid and water by reflux. In a further embodiment, R$_1$ and R$_2$ are Br.

In a further embodiment, the compound with the structure

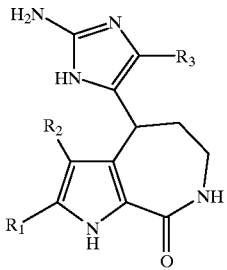

is produced by a process comprising reacting a compound with the structure of:

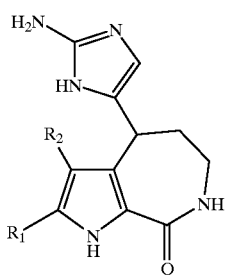

with acetic acid and water by reflux.

In a further embodiment, the second compound is produced by reacting a compound with the structure:

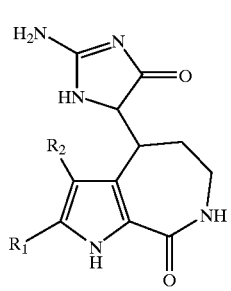

with a halogenating agent and trifluoroacetic acid at about room temperature. In a further embodiment, R$_1$ and R$_2$ are Br and the halogenating agent is Br$_2$.

In another embodiment, the second compound is produced by a process comprising reacting a compound with the structure:

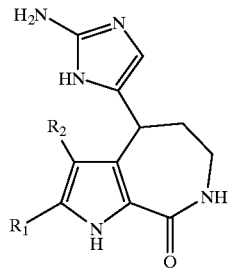

with a halogenating agent and CH$_3$SO$_3$H at about room temperature. In a further embodiment, R$_1$ and R$_2$ are Br and the halogenating agent is Br$_2$.

This invention provides a process for producing hymenialdisine, wherein the process comprises reacting a compound with the structure of

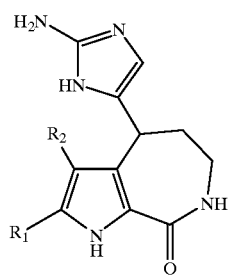

with CH$_3$SO$_3$H and catalytic HBr at about 90° C. in a sealed tube for about 12 hours. In a further embodiment R$_1$ and R$_2$ are Br.

In a further embodiment, the compound of claim 11 is produced by a process comprising reacting the compound of claim 5 with acetic acid and water by reflux.

The invention further provides a process for producing hymenialdisine by reacting a compound with the structure:

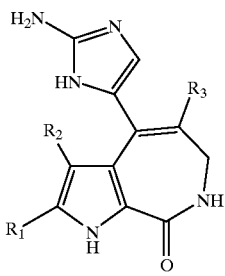

where $R_1$ and $R_2$ are Br and $R_3$ is H, with $CH_3SO_3H$ and catalytic HBr at about 90° C. in a sealed tube for about 12 hours.

Experimental Details

The synthesis of $C_{11}N_5$ marine sponge alkaloids (±)-hymenin (1), stevensine (2), hymenialdisine (3), and debromohymenialdisine (4) is described. These natural products are the primary family members of the sponge metabolites that contain a fused pyrrolo[2,3-c]azepin-8-one ring system with either a 2-aminoimidazole (AI) or glycocyamidine appendage. The key steps in the synthesis centered around the generation of novel azafulvenium ions and their regioselective heterodimerization with AI in order to create the tricyclic core. A rarely used protodebromination/oxidation strategy was employed to selectively generate the desired a-bromo substitution pattern seen in hymenialdisine (3). In addition, the AI moiety was shown to be a useful precursor to the glycocyamidine unit found in 3 and 4, which suggests that AI derived natural products may be the biogenic forerunners to glycocyamidine metabolites.

Synthesis of (±)-Hymenin (1)

Hymenin (1) was isolated from an Okinawan sponge, Hymeniacidon sp. Pharmacological studies have shown that 1 possesses potent a-adrenoceptor blocking properties.[2,11] We have recently completed a synthesis of racemic 1.[12] The key step in the synthesis was the preferential heterodimerization of two different heterocyclic units under acidic conditions, namely, azafulvene intermediate A and 2-aminoimidazole (AI). This coupling strategy allowed for the successful creation of the carbon-carbon bond that connects the two heterocyclic moieties of the natural product. Critical to the success of this approach was the suppression of monomer self-dimerization, which is commonly observed for pyrroles and indoles.[13]

Initial investigations were focused around the generation of azafulvenium ion A by two possible alternatives. The first involved cyclization of alcohols 5 and 10, which would then be followed by oxidation to intermediate A, while the second approach simply entailed the reversal of the cyclization and oxidation steps. In addition to contemplating strategies for the construction of the bicyclic pyrrolo[2,3-c]azepin-8-one ring system, the incorporation of Br into the pyrrole was also considered. In principle, this could be accomplished early or late in the synthesis from a requisite debromo pyrrole precursor.

Early investigations focused around the acid-promoted cyclization of the debromopyrrole derivative, 7 (Scheme 1). This compound was prepared in two ways from the corresponding alcohol 5 and dioxolane 6. Treatment of aldehyde 7 with trifluoroacetic acid (23°C., 3 d) afforded the desired bicyclic pyrrole 8 but only in 11% yield. The major product from the reaction was homodimer 9 which resulted from self-dimerization of 8 via azafulvene intermediate A (R=H). All attempts to effect mixed dimerization of 8 and AI under acidic conditions to give debromohymenin were unsuccessful. Self-dimerization of 8 to 9 was a competitively superior process to the mixed-dimerization between 8 and AI. It became clear that in order for hetero-dimerization to compete effectively, the self-dimerization tendency of pyrrole 8 would have to be inhibited. This suggested the early introduction of Br in the synthesis since the presence of Br would serve to block the nucleophilic pyrrole site such that it would retard self-dimerization processes. This indeed proved to be the case. Treatment of 2,3-dibromotrichloroacetyl pyrrole[14] with aminodioxolane[15] gave pyrrole 11 in excellent yield. Removal of the acetal group gave aldehyde 12. Treatment of 12 with methanesulfonic acid at room temperature for 7 d afforded bicyclic pyrrole 13 in good yields without the formation of homodimer. Alternatively, when cyclization of alcohol 10 was attempted prior to oxidation to the aldehyde, functionality led to dihydrooxazoline 14 was produced as the major product. No products resembling a fused bicyclic pyrrole system were detected.

The final task remaining in the synthesis of hymenin (1) involves the generation and regioselective heterodimerization of azafulvenium ion A with AI. Unlike debromo derivative 8, which failed because of self-dimerization, dibromo derivative 13 underwent smooth coupling with AI in methanesulfonic acid (23° C., 7d). After work-up and chromatography, a 65% yield of racemic hymenin (1) was obtained. All spectral data of synthetic 1 were in complete agreement with those reported for the natural product. Hydrogenation of 1 over Pd/C and NaOAc in methanol afforded (±)-2,3-debromohymenin (15) in quantitative yield.

Synthesis of Stevensine (2)

In light of the results obtained during the synthesis of (±)-hymenin (1), the general strategy for the formation of stevensine (2) (from an unidentified Micronesian sponge[3] and a New Caledonian sponge, *Pseudaxinyssa cantharella*[4]) centered around the generation of bridged bromonium ion B and/or azafulvenium ion C. These key intermediates are the oxidized forms of intermediate A (R=Br) from which racemic 1 was prepared. The coupling of intermediate B and/or C with AI followed by elimination of HBr would result in the formation of stevensine (2). Following this line of research, addition of bromine to pyrroloazepine 13 in methanol afforded a high yield of adduct 16 (Scheme 2). The next task was to effect the coupling of 16 and AI. Initially, this was attempted using trifluoroacetic acid. After stirring for 3 d, product 18[16] was obtained in 50% yield along with unreacted starting material. Addition of the exocyclic $NH_2$ group of AI to intermediate B and/or C accounts for the formation of 18. Interestingly, no products resulting from carbon-carbon bond formation were detected using trifluoroacetic acid as the proton source.

On the other hand, when methanesulfonic acid was used, the thermodynamically more stable carbon-carbon coupling product 19[17] was obtained in 46% yield together with bromo olefin 17 (20%). The elimination product, 17, can also be prepared directly by exposure of 16 to methanesulfonic acid at room temperature. Although (±)-hymenin (1) could be synthesized from the acid facilitated coupling of olefin 13 and AI, no reaction ensued upon combining bromo olefin 17 with AI under analogous conditions. These results indicate that bromo olefin 17, unlike olefin 13 and bromo ether 16, is unreactive towards AI. One possible explanation for the non-reactivity of 17 is that the formation of intermediate B/C is unfavorable from olefin 17.[18] On the other hand, the generation of the reactive charged intermediate, B and/or C, from bromo ether 16 takes place by a different mechanism, which possibly involves neighboring group activation. This conclusion is further supported by the fact that the related reaction between pyrroloazepine 13 and AI in a less acidic medium ($CF_3CO_2H$) did not occur, whereas, the use of bromo ether 16 afforded the N-C coupling product, 18.

With precursor 19 in hand, all that remained in the synthesis of stevensine (2) was the elimination of HBr. The direct removal of HBr involves a syn elimination event, a process that proved troublesome when tried under basic conditions. Therefore, an acid promoted elimination was attempted since the salts of AI heterocycles are generally quite stable. Heating 19 in methanesulfonic acid (90° C., sealed flask, 12 h) afforded products 3-debromostevensine (20) and 5-bromo-3-debromostevensine (21) in 14% and 47% yields, respectively (Scheme 3).[19] The molecular skeleton of 20 and 21 was established by hydrogenation to 2,3-debromohymenin (15). The bromo substitution pattern in 20 and 21 was deduced from their $^1H$ NMR spectra. The a-bromo substituted pyrrole showed b-pyrrole hydrogens at 6.42 (s) ppm and 6.10 (s) ppm for 20 and 21 in $CD_3OD$, respectively.

Generally, a-pyrrole hydrogens for these types of compounds typically reside around 6.9 ppm. The slight downfield shift for the b hydrogen of 20 compared to 21 is probably a reflection of a more planar arrangement of the AI ring in 20 with respect to the bicyclic core. An HMQC experiment with 21 indicated that the hydrogen at 6.10 ppm was correlated to the carbon at 113.1 ppm. This confirmed the assignment of the bromine atom as a substituted, since 113.1 ppm corresponds to an unsubstituted b pyrrole carbon within these systems. For an unsubstituted a pyrrole carbon, the chemical shift is around 120 ppm. The formation of 20 and 21 involved initial elimination of HBr from 19 to produce stevensine (2). In the presence of HBr, which can function as a reducing agent,[20] a series of chemical events took place that included protodebromination of the b-pyrrole position. This led to olefin 20 together with the production molecular bromine. Subsequent bromination of 20 generated bromo olefin 21.

At this point, a similar thermal elimination of HBr from 19 was attempted under conditions that would facilitate the removal of HBr from the reaction mixture (Scheme 3). The removal of HBr would effectively eliminate the protodebromination process and allow for the formation of stevensine (2). This indeed proved to be the case. When 19 was heated in methanesulfonic acid (90° C.) using an unstoppered flask, the HBr generated from the thermal elimination of 19 volatilized from the reaction mixture and stevensine (2) was obtained in 61% yield as a colorless solid. All spectral data of synthetic 2 were in complete agreement with those reported for the natural product. Stevensine (2) also can be prepared directly in 30% yield by heating 16 and AI in $CH_3SO_3H$ in an unsealed flask.

As an alternate approach to stevensine (2), the direct oxidation of hymenin (1) to 2 was attempted (Scheme 4). After several trials with various oxidants that included $Br_2$, $Hg(OAc)_2$, $Pb(OAc)_4$, and $FeSO_4$, this transformation was not accomplished. Treatment of 1 with 1.2 equivalents of bromine in trifluoroacetic acid cleanly afforded the expected product, 4'-bromohymenin (22) (95% yield). On the other hand, when the bromination was carried out in methanesulfonic acid using 1.2 eq. of $Br_2$, not only was 22 (21% yield) produced, but also 5-bromostevensine (23) (38% yield) and starting material were isolated from the reaction mixture. The formation of 23 is thought to arise from ipso attack[21] by $Br^+$ followed by elimination of HBr and aromatization to stevensine (2). The additional reaction of 2 with $Br_2$ produced 23. Stevensine (2) could not be obtained directly from 1 by oxidation with $Br_2$ due to the fact that the bromination of 2 to 23 proceeds faster than the bromination of 1. Protodebromination/oxidation of 22 in $CH_3SO_3H$ gave stevensine (2) in 20% yield.[19]

Synthesis of Hymenialdisine (3) and Debromohymenialdisine (4)

Since its first appearance from the Great Barrier Reef sponge *Phakellia flabellata*,[9] debromohymenialdisine (4) has been isolated along with hymenialdisine (3) from a number of different sponges.[4–9] Both 3 and 4 have been reported to possess potent antineoplastic properties.[8] A general characterization of these and numerous other marine metabolites can be made on the presence of brominated heterocyclic moieties that include pyrrole, indole, and b-carboline units. Brominated 2-aminoimidazole derivatives, interestingly enough, are not found in nature, but rather, appear to serve as progenitors to their hydrolyzed derivatives such as the glycocyamidine moieties seen in metabolites 3 and 4. Such heterocyclic functionality is common among the $C_{11}N_5$ and related metabolites isolated from sponges.[1] Hymenialdisine (3) is the only member of the $C_{11}N_5$ and dimerically related group of sponge metabolites that contains a monobromo substituted pyrrole wherein the Br atom is substituted in the a position. Based on these features, a synthetic plan was formulated that called for the development of methodology that would allow for both the preparation of the glycocyamidine moiety and the incorporation of Br in the a position of the pyrrole.

With the establishment of a synthetic route to (±)-hymenin (1) and stevensine (2), consideration of an analogous plan to 3 and 4 involved the coupling of glycocyamidine with intermediates A or B. All attempts, however, to couple glycocyamidine with olefin 13 or 16 were unsuccessful. A similar finding has been reported in the attempted condensation of glycocyamidine with ketones.[22] These results forced a change in strategy for the creation of the desired 2-aminoimidazolone functionality that involved a direct modification of the AI nucleus within an intact tricyclic system. In principle, both 3 and 4 could be derived from a suitable precursor such as 4'-bromohymenin (22) by hydrolysis, protodebromination, and side-chain oxidation (ipso bromination). Additionally, the synthesis of 3 from 22 requires a regioselective protodebromination event wherein the Br atom substituted in the b position of the pyrrole moiety is selectively removed. Based on previous transbromination findings described herein and elsewhere,[19] this approach appeared highly applicable to the present system. Initially, 22 was heated in 48% HBr (90° C., 4 h, sealed flask) and debromohymenialdisine (4) was formed directly in 40% yield together with 2,3-debromostevensine (24) (21% yield) (Scheme 5). Hymenialdisine (3), however, could not be obtained under these conditions. The formation of 4 and 24 resulted from a competition between hydrolysis and protodebromination of the brominated AI ring in 22. This led to the imidazolone and AI ring moieties of 4 and 24, respectively. Further protodebromination of the pyrrole ring produced the debromopyrrole and $Br_2$. Subsequent oxidation by $Br_2$ afforded 4 and 24. Similarly, treatment of hymenin (1) with HBr also produced products 4 and 24, but in lower yield.

A successful route to hymenialdisine (3) from precursor 22 necessitates a regioselective protodebromination event at the b position of the pyrrole system in addition to unmasking the imidazolone synthon. Despite an extensive search for suitable reaction conditions that would accommodate both obligations in a single step, none were found. Various concentrations of aqueous HBr were tested under a variety of conditions but the formation of 3 could not be detected.

Using a milder reaction medium such as a 1:1 mixture of $H_2O/CH_3CO_2H$ (120–130° C., 12 h), the hydrolysis product, 3-bromo-4,5'-dihydrohymenialdisine (25) was isolated in 72% yield as a mixture of diastereomers (Scheme 5). The objective now became to effect a regioselective protodebromination of 25. In related studies on the protodebromination of pyrroles 19 (vide infra) and 22,[19] both derivatives were shown to undergo regioselective protodebromination at the b position of the pyrrole ring upon heating in $CH_3SO_3H$. Under these conditions, HBr was generated in situ (from 19 or 22) in a highly controlled manner that served to effect a selective protodebromination at the more reactive b site. This result suggested that a similar protodebromination could occur with 25 in $CH_3SO_3H$ if one controls the amount of HBr present. When 25 was exposed to $CH_3SO_3H$ (90° C., 12 h) containing a catalytic amount of HBr, hymenialdisine (3) and debromohymenialdisine (4) were produced in 33% and 27% yields, respectively. Moreover, these conditions allowed for a concomitant protodebromination and oxidation event that led to the a, b-unsaturated 2-aminoimidazolone system of 3 and 4. No evidence of diastereomer formation about the imidazolone double bond was found. All spectral data of synthetic 3 and 4 were in complete agreement with those reported for the natural product. The configuration seen in natural products 3 and 4 appear to be that which is thermodynamically most stable. Alternatively, hydrolysis (120° C., 3 d) of 5-bromo-3-debromostevensine (21) in aq. $CH_3CO_2H$ gave hymenialdisine (3) (65% yield) as the major product.

The $^1H$ NMR spectra of hymenialdisine (3) is noteworthy in terms of previously published data for the natural product. The structure of natural 3 was firmly established by X-ray analysis. The $^1H$ NMR spectrum (DMSO-$d_6$) of the free base of 3 has been reported[5] wherein the b-pyrrole hydrogen was assigned to 7.28 ppm. Interestingly, while the HCl salt of synthetic 3 behaved consistently in both $D_2O$ and DMSO-$d_6$ the spectrum of the free base did not. Hymenialdisine (3)-HCl showed sharp signals at 6.62 and 6.64 ppm for b pyrrole hydrogens, respectively. The free base, on the other hand, gave a hump instead of a singlet around 6.60 ppm in $D_2O$ which shifted downfield to 7.28 ppm in DMSO-$d_6$. A similar phenomenon was observed for 4.23 The underlying reasons for these observations are unknown but may reflect a conformational dependency of the molecule on solvent.

With the ready availability of debromohymenialdisine (4), the mono bromination of this derivative was investigated. This was done in order to determine the regioselectivity of the bromination (Scheme 6). When 4 was treated with 1 eq of NBS (or $Br_2$), 3-bromo-2-debromohymenialdisine (26) was produced as the major product. The a-bromo regioisomer corresponding to the natural product, 3, was not detected. As with protodebromination, bromination also took place selectively at the b-position. This is consistent with previous results that indicate the b-position of these 2-acyl pyrrole systems is generally the more reactive site.[24] Furthermore, the favorable b bromination most likely accounts for the formation of the majority of monobromo $C_{11}N_5$ and related series of marine alkaloids isolated to date.[1] These results may have implications for the biosynthesis of 3 especially when one considers the timing and formation of the a-bromopyrrole moiety. One speculation consistent with the above chemistry would be an early incorporation of two Br atoms to the pyrrole and selective removal of one Br at the more reactive b site.

In conclusion, this invention shows a short synthesis of the $C_{11}N_5$ pyrrolo-lactam family of marine sponge alkaloids. The brevity of the syntheses was made possible by devising approaches and suitable reaction conditions that avoid the use of protecting groups, particularly those for nitrogen. The key steps centered around a coupling strategy between novel azafulvene precursors and 2-aminoimidazole (AI) to create the tricyclic core. A rarely used protodebromination/oxidation strategy was employed to selectively generate the desired a-bromo substitution pattern seen in hymenialdisine (3). While explicit here, this process should have additional applications to a variety of marine alkaloids containing brominated heterocycles that include indoles, pyrroles, and tyrosine derivatives.

Unless otherwise noted, materials were obtained from common commercial suppliers and used without further purification, except solvents which were dried and distilled. $^1H$ NMR spectra were measured on a Varian VXR 400 MHz spectrometer. Residual solvent signals were used as references. $^{13}C$ NMR spectra were recorded on a Varian VXR 300 spectrometer at 75 MHz. For the attached proton test (APT), "e" represents signals for C and $CH_2$ carbons and "o" for CH and $CH_3$ carbons. Chemical ionization (CI) and electron impact (EI) mass spectra were obtained on a Nermag R-10-10-10 quadrupole mass spectrometer. Chemical ionization was performed using either $CH_4$ or $NH_3$ gas. Fast atom bombardment (FAB) mass spectra were obtained on a JEOL DX303HF spectrometer. HCl salts of compounds were made by the addition of 10% HCl to the free base followed by concentration in vacuo. Combustion analyses were performed at the Analytical Facility, Columbia University.

N-(3-Hydroxypropyl)pyrrole-2-carboxamide (5). To a stirred solution of 3-hydroxylpropylamine (1.2 g, 16.2 mmol) in 50 mL of acetonitrile was added of 2-pyrroltrichloromethyl ketone[25] (2.9 g, 13.5 mmol) at room temperature. After 16 h, the reaction mixture was concentrated under reduced pressure and the resulting residue was purified by flash chromatography ($CH_2Cl_2$/MeOH 19:1) to give 5 (2.0 g, 88%) as a colorless solid: mp 71–73° C.; $^1H$ NMR ($CDCl_3$) d 1.77 (p, 2H, J=5.7), 2.30 (bs, 1H), 3.59 (q, 2H, J=5.7), 3.69 (t, 2H, J=5.7), 6.23 (m, 1H), 6.28 (br, 1H), 6.56 (m, 1H), 6.94 (m, 1H), 9.45 (bs, 1H); $^{13}C$ NMR ($CDCl_3$) d 32.4 (e), 36.3 (e), 59.5 (e), 109.3 (o), 109.8 (o), 121.9 (o), 125.5 (e), 162.3 (e); IR (nujol) 1607, 1577, 1531, 1426, 1336, 1215 $cm^{-1}$; MS m/z (relative intensity) 169 ($M^++1$, 100), 151 (30), 124 (35), 94 (78); Anal. Calcd for $C_8H_{12}N_2O_2$: C, 57.13; H, 7.19; N, 16.66; Found: C, 57.01; H, 7.29; N, 16.53.

N-[2-(1,3-Dioxolan-2-yl)ethyl]pyrrole-2-carboxamide (6). To a stirred solution of 2-(2-aminoethyl)-1,3-dioxolane[5] (2.4 g, 20.6 mmol) in 30 mL of acetonitrile was added 2-pyrrol trichloromethyl ketone (4.3 g, 20.5 mmol) at room temperature. After 16 h, the reaction mixture was concentrated under reduced pressure and the residue was purified by flash column chromatography ($CH_2Cl_2$/MeOH 19:1) to give 6 (3.8 g, 88%) as a colorless solid: mp 133–135° C.; $^1H$ NMR ($CDCl_3$) d 1.99 (dt, 2H, J=6.0, 4.3), 3.58 (dt, 2H, J=6.0, 5.7), 3.91 (m, 2H), 4.04 (m, 2H), 5.01 (t, 1H, J=4.3), 6.23 (m, 1H), 6.52 (m, 1H), 6.63 (br, 1H), 6.91 (m, 1H), 9.57 (br, 1H); $^{13}C$ NMR ($CDCl_3$) d 32.7 (e), 34.6 (e), 65.0×2 (e), 103.9 (o), 108.6 (o), 109.5 (o), 121.4 (o), 126.3 (e), 161.1 (e); IR (nujol) 1615, 1530, 1476, 1327, 1202, 1151 $cm^{-1}$; MS m/z (relative intensity) 211 ($M^++1$, 100), 149 (21), 138 (15), 123(25), 96(10); Anal. Calcd. for $C_{10}H_{14}N_2O_3$: C, 57.13; H, 6.71; N, 13.32; Found: C, 57.24; H, 6.79; N, 13.13.

N-(3-Oxopropyl)pyrrole-2-carboxamide (7). Method A. A mixture of 6 (2.85 g, 13.6 mmol) and p-toluenesulfonic acid monohydrate (1.3 g, 6.84 mmol) in 80 mL of acetone/water (1:1, v/v) was refluxed for 6 h. After cooling, the reaction mixture was extracted with $CH_2Cl_2$ (3×100 mL). The combined organic extracts were dried ($MgSO_4$) and concentrated under reduced pressure. The resulting solid was recrystallized from acetone/$CH_2Cl_2$ to afford 7 (1.81 g, 80%) as a colorless solid: mp 88–90° C.; $^1H$ NMR ($CDCl_3$) d 2.77 (t, 2H, J=5.8), 3.66 (q, 2H, J=5.8), 6.16 (m, 1H), 6.38 (br, 1H), 6.50 (m, 1H), 6.87 (m, 1H), 9.69 (br, 1H), 9.78 (bs, 1H); $^{13}C$ NMR ($CD_3COCD_3$) d 33.7 (e), 44.6 (e), 109.6 (o), 110.0 (o), 122.1 (o), 127.1 (e), 162.0 (e), 201.9 (o); IR (nujol) 1715, 1622, 1565, 1409, 1328 $cm^{-1}$; MS m/z (relative intensity) 167 ($M^+$+1, 100), 138 (15), 123 (28), 94 (50); Anal. Calcd for $C_8H_{10}N_2O_2$: C, 57.82; H, 6.07; N, 16.86; Found: C, 57.68; H, 5.17; N, 16.79. Method B. To a stirred solution of oxalyl chloride (0.12 mL, 1.31 mmol) in 3 mL of $CH_2Cl_2$ at −78° C. was added DMSO (0.21 mL, 2.9 mmol) in 0.6 mL of $CH_2Cl_2$ under argon. After 2 min, a solution of 5 (0.2 g, 1.19 mmol) in 40 mL of $CH_2Cl_2$ was added to the mixture and allowed to stir for 15 min. Next, triethylamine (830 mL, 5.92 mmol) was added and the reaction mixture was allowed to warm to room temperature. After 15 min, the mixture was poured into 10 mL of water and the organic layer was separated and washed successively with 10% citric acid (20 mL), saturated $NaHCO_3$ (20 mL), and saturated NaCl (20 mL). The organic layer was dried ($MgSO_4$) and concentrated under reduced pressure. The resulting residue was purified by flash column chromatography ($CH_2Cl_2$/MeOH 19:1) to afford 7 (0.14 g, 70%) as a colorless solid.

6,7-Dihydro-1H-pyrrolo[2,3-c]azepin-8-one (8) and dimer 9. A solution of 7 (1.0 g, 6.0 mmol) in 10 mL of $CF_3COOH$ was stirred at room temperature for 3 d. The reaction mixture was concentrated under reduced pressure and the resulting residue was purified by flash chromatography ($CH_2Cl_2$/MeOH saturated with $NH_3$ 19:1) to afford 8 (0.10 g, 11%) and then 9 (0.52 g, 59%) as colorless solids. 8: mp 155–160° C.; $^1H$ NMR ($CD_3OD$) d 3.54 (d, 2H, J=6.3), 5.86 (dt, 1H, J=9.7, 6.3), 6.21 (d, 1H, J=2.6), 6.76 (d, 1H, J=9.7), 7.01 (d, 1H, J=2.6); ($CDCl_3$) d 3.65 (t, 2H, J=6.4), 5.87 (dt, 1H, J=10.0, 6.4), 6.24 (t, 1H, J=2.6), 6.38 (br, 1H), 6.77 (d, 1H, J=10.0), 6.99 (t, 1H, J=2.6), 10.46 (br, 1H); $^{13}C$ NMR ($CD_3OD$) d 40.0 (e), 110.0 (o), 123.8 (o), 124.1 (o), 125.8 (e), 127.7 (e), 129.3 (o), 166.7 (e); IR (nujol) 3307, 1647, 1488, 1421, 1328, 1164 $cm^{-1}$; UV ($CH_3OH$) $1_{max}$ 276, 223 nm; MS m/z (rel. intensity) 148 ($M^+$, 100), 119 (45), 105 (10), 92 (40); HRMS, calcd for $C_8H_8N_2O$ 148.0637, found 148.0638. 9: mp 199–201° C.; $^1H$ NMR ($CD_3OD$) d 2.16 (dt, 2H, J=6.1, 5.3), 3.22 (m, 2H), 3.44 (d, 2H, J=6.6), 4.33 (t, 1H, J=6.1), 5.73 (s, 1H), 5.73 (dt, 1H, J=9.9, 6.6), 5.88 (d, 1H, J=2.6), 6.56 (d, 1H, J=9.9), 6.83 (d, 1H, J=2.6); $^{13}C$ NMR ($CD_3OD$) d 35.3, 38.9, 40.0, 40.3, 108.9, 112.5, 123.0, 123.5, 123.8, 124.5, 127.4, 128.1, 129.3, 143.4, 166.4, 166.8; (DMSO-$d_6$) 34.8 (e), 37.7 (o), 38.1 (e), 38.3 (e), 107.7 (o), 111.3 (o), 122.1 (o), 123.3 (e), 123.9 (o), 124.8 (e), 125.0 (e), 127.2 (e), 128.1 (o), 142.0 (e), 164.1 (e), 164.5 (e). IR (nujol) 3200, 1622, 1558, 1485, 1271, 1211 $cm^{-1}$; UV ($CH_3OH$) $1_{max}$ 271, 226 nm; MS m/z (rel. intensity) 296 ($M^+$, 100), 253 (65), 224 (45), 196 (30), 167 (40); HRMS, calcd for $C_{16}H_{16}N_4O_2$ ($M^+$) 296.1273, found 296.1281. Anal. Calcd for $C_{16}H_{16}N_4O_2$: C, 64.85; H, 5.44; N, 18.91. Found: C, 64.94; H, 5.53; N, 18.83.

4,5-Dibromo-N-(3-hydroxypropyl)pyrrole-2-carboxamide (10). To a stirred solution of 3-hydroxylpropylamine (1.2 g, 16.2 mmol) in 50 mL of acetonitrile was added 4,5-dibromopyrrol-2-yl trichloromethyl ketone[14] (5.0 g, 13.5 mmol) at room temperature. After 16 h, the reaction mixture was filtered and the precipitate 10 (4.2 g, 96%) was collected as a colorless solid: mp 160–162° C.; $^1H$ NMR ($CD_3COCD_3$) d 1.73 (p, 2H, J=6.5), 3.47 (q, 2H, J=6.5), 3.60 (bs, 2H), 3.81 (bs, 1H), 6.88 (d, 1H, J=2.9), 7.67 (bs, 1H), 11.84 (br, 1H); $^{13}C$ NMR ($CD_3COCD_3$) d 33.4 (e), 37.1 (e), 59.9 (e), 99.4 (e), 105.2 (e), 113.0 (o), 129.2 (e), 160.4 (e); IR (nujol) 3285, 1608, 1579, 1531, 1247 $cm^{-1}$; UV ($CH_3OH$) $1_{max}$ 274, 232, 210 (sh) nm; MS m/z (relative intensity) 329 ($M^+$+5, 50), 327 ($M^+$+3, 100), 325 ($M^+$+1, 50), 309 (15); Anal. Calcd for $C_8H_{10}N_2O_2Br_2$: C, 29.48; H, 3.09; N, 8.59; Found: C, 29.60; H, 3.14; N, 8.35.

4,5-Dibromo-N-[2-(1,3-dioxolan-2-yl)ethyl]pyrrole-2-carboxamide (11). A solution of 2-(2-aminoethyl)-1,3-dioxolane (2.4 g, 20.6 mmol) and 4,5-dibromopyrrol-2-yl trichloromethyl ketone (7.6 g, 20.5 mmol) in 30 mL of acetonitrile was stirred at room temperature for 16 h. The reaction mixture was filtered and the precipitate 11 (6.8 g, 90%) was collected as a colorless solid: mp 155–157° C.; $^1H$ NMR ($CDCl_3$) d 1.99 (dt, 2H, J=6.0, 4.2), 3.61 (dt, 2H, J=6.0, 5.6), 3.92 (m, 2H), 4.05 (m, 2H), 5.00 (t, 1H, J=4.2), 6.51 (d, 1H, J=2.8), 6.66 (bs, 1H), 10.57 (bs, 1H); $^{13}C$ NMR ($CD_3COCD_3$) d 34.3 (e), 35.5 (e), 65.4×2 (e), 99.4 (e), 103.4 (o), 105.4 (e), 113.0 (o), 129.1 (e), 160.0 (e); IR (nujol) 3358, 1646, 1569, 1412, 1372 $cm^{-1}$; UV ($CH_3OH$) $1_{max}$ 275, 233, 214 (sh) nm; MS m/z (relative intensity) 371 ($M^+$+5, 50), 369 ($M^+$+3, 100), 367 ($M^+$+1, 50), 289 (13), 118 (25), 101 (50), 73 (30); Anal. Calcd for $C_8H_{10}N_2O_2Br_2$: C, 32.63; H, 3.29; N, 7.61; Found: C, 32.77; H, 3.17; N, 7.51.

4,5-Dibromo-N-(3-oxopropyl)pyrrole-2-carboxamide (12). A mixture of 11 (5.0 g, 13.6 mmol) and p-toluenesulfonic acid monohydrate (1.3 g, 6.84 mmol) in 80 mL of acetone/water (1:1) was refluxed for 12 h. After cooling, the reaction mixture was extracted with $CH_2Cl_2$ (3×100 mL). The combined organic extracts were dried ($MgSO_4$) and concentrated under reduced pressure. The resulting solid was recrystallized from acetone/$CH_2Cl_2$ to afford 12 (4.0 g, 91%) as a colorless solid: mp 160–163° C.; $^1H$ NMR ($CD_3COCD_3$) d 2.73 (td, 2H, J=6.5, 1.5), 3.63 (q, 2H, J=6.5), 6.85 (d, 1H, J=2.9), 7.63 (br, 1H), 9.75 (t, 1H, J=1.5), 11.73 (br, 1H); $^{13}C$ NMR ($CD_3COCD_3$) d 33.9 (e), 44.3 (e), 99.5 (e), 105.6 (e), 113.3 (o), 128.8 (e), 160.3 (e), 201.6 (o); IR (nujol) 3212, 1715, 1610, 1561 $cm^{-1}$; MS, m/z (relative intensity) 327 ($M^+$+5, 50), 325 ($M^+$+3, 100), 323 ($M^+$+1, 50), 247 (25), 226 (22), 171 (20), 127 (19); Anal. Calcd for $C_8H_8N_2O_2Br_2$: C, 29.66; H, 2.49; N, 8.65; Found: C, 29.49; H, 2.57; N, 8.53.

2,3-Dibromo-6,7-dihydro-1H-pyrrolo[2,3-c]azepin-8-one (13). A solution of 12 (1.0 g, 3.3 mmol) in 10 mL of methanesulfonic acid was stirred at room temperature for 7 d. The reaction mixture was diluted with ether (500 mL), washed with sat. $NaHCO_3$ (100 mL ×3) and sat. NaCl (100 mL). The organic layer was dried ($MgSO_4$) and evaporated under reduced pressure. The resulting residue was purified by flash chromatography ($CH_2Cl_2$/MeOH 19:1) to give 13 (0.68 g, 80%) as a colorless solid: mp 170–175° C.; $^1H$ NMR ($CD_3OD$) d 3.57 (d, 2H, J=6.4), 6.01 (dt, 1H, J=10.1, 6.4), 6.65 (d, 1H, J=10.1); (DMSO-$d_6$) d 3.46 (dd, 2H, J=6.4, 4.9), 6.03 (dt, 1H, J=10.0, 6.4), 6.54 (d, 1H, J=10.0), 7.75 (t, 1H, J=4.9), 13.04 (s, 1H); $^{13}C$ NMR ($CD_3OD$) d 39.6 (e), 100.2 (e), 108.4 (e), 126.4 (o), 126.7 (e), 126.8 (o), 127.0 (e), 164.6 (e); IR (nujol) 3184, 1639, 1603, 1541 $cm^{-1}$; UV ($CH_3OH$) $1_{max}$ 288, 227 nm; MS, m/z (relative intensity) 308 ($M^+$+4, 30), 306 ($M^+$+2, 60), 304 ($M^+$, 30), 225 (100), 200 (80), 182 (40), 170 (40); HRMS, calcd for $C_8H_6N_2OBr_2$ ($M^+$) 303.8847, found 303.8833. Anal. Calcd for $C_8H_6N_2OBr_2$: C, 34.41; H, 1.98; N, 9.16; Found: C, 34.75; H, 2.09; N, 9.07.

2-(2,3-Dibromopyrrol-5-yl)-1,3-oxazoline (14). Method A. A solution of 10 (0.25 g, 0.77 mmol) in 2 mL of methanesulfonic acid was heated at 60° C. for 3 d. The reaction mixture was diluted with ether (100 mL) and washed with sat. NaHCO$_3$ (20 mL×3) and sat. NaCl (20 mL). The organic layer was dried (MgSO$_4$) and evaporated under reduced pressure. The resulting residue was purified by flash chromatography (EtOAc/hexanes 1:1) to give 14 (0.14 g, 59%) as a colorless solid: $^1$H NMR (CDCl$_3$) d 2.00 (p, 2H, J=5.7), 3.52 (t, 2H, J=5.7), 4.32 (t, 2H, J=5.7), 6.58 (s, 1H), 10.10 (br, 1H); $^{13}$C NMR (CD$_3$COCD$_3$) d 22.2 (e), 41.3 (e), 66.6 (e), 99.1 (e), 109.4 (e), 115.0 (o), 127.7 (e), 153.8 (e); UV (CH$_3$OH) 1$_{max}$ 329, 275 nm; MS m/z (relative intensity) 311 (M$^+$+5, 50), 309 (M$^+$+3, 100), 307 (M$^+$+1, 50); Anal. Calcd for C$_8$H$_8$N$_2$OBr$_2$: C, 31.20; H, 2.62; N, 9.10; Found: C, 31.17; H, 2.51; N, 9.29. Method B. To a stirred mixture of 10 (0.25 g, 0.77 mmol) and p-toluenesulfonyl chloride (0.16 g, 0.77 mmol) in 10 mL of THF was added triethylamine (0.6 mL, 4.27 mmol) at room temperature. The mixture was heated at 80° C. overnight. The solvent was evaporated under reduced pressure and the resulting residue was purified by flash chromatography (CH$_2$Cl$_2$/MeOH 19:1) to give 14 (0.15 g, 63%) as a colorless solid.

(±)-Hymenin (1). A solution of 13 (1.0 g, 3.3 mmol) and 2-aminoimidazole (AI) sulfate (0.52 g, 4.0 mmol) in 5 mL of methanesulfonic acid was stirred for 7 d at room temperature. Ether was added to the reaction mixture (50 mL×5), decanted, and the resulting residue dissolved in 1 mL of MeOH and left standing overnight. The resulting precipitate was filtered and washed with methanol (2×2 mL) to afford the methanesulfonic acid salt of 1 (1.0 g, 65%) as a colorless solid. The free base of 1 was generated by passing the salt of 1 through a short plug of silica (CH$_2$Cl$_2$/MeOH sat. NH$_3$ 8:2) and obtained as a colorless solid: $^1$H NMR (CD$_3$OD) d 1.98 (ddd, 1H, J=14.6, 10.0, 4.0), 2.35 (ddd, 1H, J=14.6, 7.0, 4.0), 3.14 (dd, 1H, J=14.6, 7.0), 3.26 (dd, 1H, J=14.6, 10.0), 4.09 (t, 1H, J=4.0), 5.80 (s, 1H); 13C NMR (CD$_3$OD) d 32.7 (e), 37.9 (e), 38.4 (o), 102.8 (e), 107.7 (e), 113.0 (o), 125.3 (e), 128.5 (e), 136.8 (e), 150.6 (e), 164.2 (e); IR (nujol) 3270, 1676, 1625, 1566 cm$^{-1}$; UV (CH$_3$OH) 1$_{max}$ 275 nm (e=9570); MS m/z (relative intensity) 392 (M$^+$+5, 50), 390 (M$^+$+3, 100), 388 (M$^+$+1, 50); HRMS, calcd for C$_{11}$H$_{11}$N$_5$OBr$_2$ (MH$^+$) 387.9409, found 387.9403. 1.CH$_3$SO$_3$H: $^1$H NMR (CD$_3$OD) d 2.18 (m, 1H), 2.25 (m, 1H), 2.72 (s, 3H), 3.27 (t, 2H, J=3.8), 4.23 (t, 1H, J=3.8), 6.19 (s, 1H). Anal. Calcd for C$_{11}$H$_{13}$N$_5$OBr$_2$.CH$_3$SO$_3$H: C, 29.71; H, 3.12; N, 14.44; Found: C, 29.89; H, 3.15; N, 14.37.

(±)-2,3-Debromohymenin (15). A mixture of 1 (100 mg, 0.21 mmol), sodium acetate (35 mg, 0.43 mmol) and 10% Pd/C (11 mg) in 10 mL of MeOH was stirred under 1 atm. of hydrogen at room temperature for 5 h. The reaction mixture was filtered and the filtrate evaporated under reduced pressure. The resulting residue was purified by flash chromatography (CH$_2$Cl$_2$/MeOH sat. with NH$_3$ 8:2) to afford 15 (48 mg, 99%) as a colorless solid. $^1$H NMR (CD$_3$OD) d 2.14 (ddd, 1H, J=14.6, 8.6, 5.0), 2.25 (ddd, 1H, J=14.6, 8.0, 6.7), 3.22 (dd, 1H, J=14.6, 8.0), 3.34 (dd, 1H, J=14.6, 8.6), 4.14 (dd, 1H, J=6.7, 5.0), 6.03 (d, 1H, J=2.6), 6.05 (s, 1H), 6.90 (d, 1H, J=2.6); $^{13}$C NMR (CD$_3$OD) d 34.5 (t), 39.3 (d), 40.0 (t), 112.6 (d), 112.7 (d), 123.0 (s), 123.2 (d), 130.1 (s), 138.9 (s), 150.8 (s), 166.5 (s); IR (nujol) 3114, 2753, 2464, 2118, 1598, 1410 cm$^{-1}$; UV (CH$_3$OH) 1$_{max}$ 266, 219 nm; MS m/z (relative intensity) 232 (M$^+$+1, 100), 149 (12), 117 (10). Anal. Calcd for C$_{11}$H$_{13}$N$_5$O: C, 57.13; H, 5.67; N, 30.28; Found: C, 57.45; H,5.75; N, 30.05.

Trans-2,3,5-tribromo-4-methoxy-4,5,6,7-tetrahydro-1H-pyrrolo[2,3-c]-azepin-8-one (16). To a stirred solution of 13 (5.0 g, 16.3 mmol) in 20 mL of MeOH was added Br$_2$ (1.0 mL, 19.6 mmol) at room temperature. After 20 min, the reaction mixture was concentrated under reduced pressure and the resulting residue was purified by flash chromatography (EtOAc/CH$_2$Cl$_2$ 1:1) to afford 16 (6.5 g, 95%) as a colorless solid: $^1$H NMR (DMSO-d$_6$) d 3.27 (m, 1H), 3.49 (s, 3H), 3.65 (dd, 1H, J=15.1, 2.0), 4.35 (d, 1H, J=3.1), 4.92 (dd, 1H, J=6.4, 3.1), 8.08 (dd, 1H, J=7.2, 2.0), 12.80 (s, 1H); (CD$_3$OD) d 3.39 (ddd, 1H, J=15.1, 6.6, 1.1), 3.58 (s, 3H), 3.85 (dd, 1H, J=15.1, 1.1), 4.50 (dd, 1H, J=3.3, 1.1), 4.75 (ddd, 1H, J=6.6, 3.3, 1.1); $^{13}$C NMR (DMSO-d$_6$) d 39.5 (e), 47.9 (o), 57.3 (o), 79.1 (o), 101.8 (e), 106.3 (e), 121.4 (e), 124.3 (e), 160.7 (e); IR (nujol) 3174, 1626, 1557, 1477 cm$^{-1}$; UV (CH$_3$OH) 1$_{max}$ 279, 230 nm; MS m/z (relative intensity) 421 (M$^+$+7, 33), 419 (M$^+$+5, 100), 417 (M$^+$+3, 100), 415 (M$^+$+1, 33), 389 (12), 387 (36), 385 (36), 383 (12); Anal. Calcd for C$_9$H$_9$N$_2$O$_2$Br$_3$: C, 25.93; H, 2.18; N, 6.72; Found: C, 25.84; H, 2.31; N, 6.61. 2,3,5-Tribromo-6,7-dihydro-1H-pyrrolo[2,3-c]azepin-8-one (17). A solution of 16 (1.0 g, 2.4 mmol) in 5 mL of methanesulfonic acid was stirred at room temperature for 1 d. The reaction mixture was diluted with ether (200 mL), washed with sat. NaHCO$_3$ (100 mL×3), sat. NaCl (100 mL) and dried (MgSO$_4$). Evaporation followed by flash chromatography (CH$_2$Cl$_2$/MeOH sat. with NH3 19:1) afforded 17 (88 mg, 96%) as a colorless solid: $^1$H NMR (DMSO-d$_6$) d 3.88 (d, 2H, J=4.4), 6.85 (s, 1H), 8.07 (t, 1H, J =4.4), 13.24 (s, 1H); (CD$_3$OD) d 3.87 (s, 2H), 6.88 (s, 1H); $^{13}$C NMR (DMSO-d$_6$) d 48.1 (e), 98.2 (e), 107.9 (e), 117.9 (e), 123.7 (e), 126.3 (o), 126.6 (e), 161.6 (e); IR (nujol) 3153, 1660, 1536, 1414, 1257 cm$^{-1}$; UV (CH$_3$OH) 1$_{max}$ 288, 234 nm; MS m/z (relative intensity) 388 (M$^+$+6, 33), 386 (M$^+$+4, 100), 384 (M$^+$+2, 100), 382 (M$^+$, 33); HRMS, calcd for C$_8$H$_5$N$_2$OBr$_3$ (M$^+$) 381.7952, found 381.7941. Anal. Calcd for C$_8$H$_5$N$_2$OBr$_3$: C, 24.97; H, 1.31; N, 7.28. Found: C, 25.29; H, 1.47; N, 7.25.

Trans-4-(1H-imidazol-2-yl-amino)-2,3,5-tribromo-4,5,6,7-tetrahydro-1H-pyrrolo-[2,3-c]azepin-8-one (18). A solution of 16 (1.0 g, 2.4 mmol) and AI sulfate (0.38 g, 2.9 mmol) in 5 mL of trifluoroacetic acid was stirred at room temperature for 3 d. The reaction mixture was diluted with ether (50 mL×5), decanted, and the resulting residue was purified by flash chromatography (CH$_2$Cl$_2$/MeOH sat. with NH$_3$ 9:1) afforded 18 (0.55 g, 50%) as a colorless solid: $^1$H NMR (CD$_3$OD) d 3.40 (dd, 1H, J=15.4, 6.6), 3.94 (d, 1H, J=15.4), 4.70 (dd, 1H, J=6.6, 3.4), 5.07 (d, 1H, J=3.4), 6.64 (s, 2H); $^{13}$C NMR (CD$_3$OD) d 41.6 (t), 50.3 (d), 57.9 (d), 103.3 (s), 108.3 (s), 118.3 (d×2), 124.0 (s), 125.2 (s), 149.6 (s), 163.8 (s); IR (nujol) 3240, 2921, 1671, 1566, 1406 cm$^{-1}$; UV (CH$_3$OH) 1$_{max}$ 277, 209 (sh) nm; MS m/z (relative intensity) 471 (M$^+$+6, 33), 469 (M$^+$+4, 100), 467 (M$^+$+2, 100), 465 (M$^+$, 33); HRMS, calcd for C$_{11}$H$_{10}$N$_5$OBr$_3$ (M$^+$) 464.8436, found 464.8436. Anal. Calcd for C$_{11}$H$_{10}$N$_5$OBr$_3$: C, 28.23; H, 2.15; N, 14.97. Found: C, 28.54; H, 1.95; N, 15.21.

Trans-(±)-5-bromohymenin (19). A solution of 16 (1.0 g, 2.4 mmol) and AI sulfate (0.38 g, 2.9 mmol) in 5 mL of methanesulfonic acid was stirred at room temperature for 5 d. The reaction mixture was diluted with ether (50 mL×5), decanted, and the resulting residue was purified by flash chromatography (CH$_2$Cl$_2$/MeOH sat. with NH$_3$ 9:1) afforded 19 (0.51 g, 46%) as a colorless solid. Olefin 17 (0.2 g, 20%) was obtained from the ether extracts. $^1$H NMR (DMSO-d$_6$) d 3.18 (m, 1H), 3.69 (d, 1H, J=14.6), 4.24 (bs, 1H), 4.86 (bs, 1H), 5.28 (bs, 2H), 5.95 (s, 1H), 7.91 (d, 1H, J=6.8), 10.12 (br, 1H), 12.28 (br, 1H); (CD$_3$OD) d 3.25 (dd, 1H, J=15.3, 6.1), 3.70 (d, 1H, J=15.3), 4.40 (d, 1H, J=3.2), 4.84 (dd, 1H, J=6.1, 3.2), 5.88 (s, 1H); $^{13}$C NMR (DMSO-d$_6$) d 41.1 (e), 46.4 (o), 52.2 (o), 101.1 (e), 106.1 (e), 110.2 (o), 122.3 (e), 124.3 (e), 136.0 (e), 149.8 (e), 161.2 (e); UV (CH$_3$OH) 1$_{max}$ 277, 214 nm; HRMS, calcd for C$_{11}$H$_{10}$N$_5$OBr$_3$ (M$^+$) 464.8436, found 464.8438. 19.CH$_3$SO$_3$H: $^1$H NMR (DMSO-d$_6$) d 2.39 (s, 3H), 3.25 (m, 1H), 3.49 (d, 1H, J=15.5), 4.38 (bs, 1H), 4.80 (bs, 1H), 6.40 (s, 1H), 7.53 (s, 2H), 8.04 (d, 1H, J=6.1), 11.89 (s, 1H), 12.25 (s, 1H), 12.81 (s, 1H). Anal. Calcd for C$_{11}$H$_{10}$N$_5$OBr$_3$.CH$_3$SO$_3$H: C, 25.55; H, 2.50; N, 12.42. Found: C, 25.70; H, 2.58; N, 12.31.

3-Debromostevensine (20) and 5-bromo-3-debromostevensine (21). A solution of 19 (100 mg, 0.21 mmol) in 2 mL of methanesulfonic acid was heated at 90° C. in a sealed tube for 12 h. After cooling, the reaction mixture was diluted with ether (10 mL×5), decanted, and the resulting residue was purified by flash chromatography (CH$_2$Cl$_2$/MeOH sat. with NH$_3$ 8:2) to afford 21 (38 mg, 47%) and then 20 (11 mg, 14%) both as colorless solids. 20: $^1$H NMR (CD$_3$OD) d 3.55 (d, 2H, J=7.1), 6.06 (t, 1H, J=7.1), 6.42 (s, 1H), 6.56 (s, 1H); 13C NMR (CD$_3$OD) d 39.4 (e), 105.9 (e), 112.2 (o), 116.5 (o), 118.1 (o), 127.9 (e), 128.1 (e), 132.8 (e), 133.0 (e), 151.6 (e), 165.5 (e); IR (nujol) 3178, 1615, 1480, 1423, 1268 cm$^{-1}$; UV (CH$_3$OH) 1$_{max}$ 260 (sh), 229 nm; HRMS, calcd for C$_{11}$H$_{13}$N$_5$OBr (MH$^+$) 310.0301, found 310.0300. 20.HCl: $^1$H NMR (CD$_3$OD) d 3.61 (d, 2H, J=7.0), 6.14 (t, 1H, J=7.0), 6.40 (s, 1H), 6.86 (s, 1H); $^{13}$C NMR (CD$_3$OD) d 39.3, 107.1, 111.7, 112.8, 122.5, 126.1, 127.7, 128.1, 128.7, 149.1, 164.9, UV (CH$_3$OH) 1$_{max}$ 348, 280 (sh) 236 nm. Anal. Calcd for C$_{11}$H$_{12}$N$_5$OBr.HCl: C, 38.12; H, 3.78; N, 20.20. Found: C, 38.00; H, 3.69; N, 19.87. 21: $^1$H NMR (CD$_3$OD) d 4.10 (s, 2H), 6.10 (s, 1H), 6.78 (s, 1H); (DMSO-d$_6$) d 3.94 (d, 2H, J=5.6), 5.44 (bs, 2H), 6.06 (s, 1H), 6.71 (s, 1H), 8.22 (t, 1H, J=5.6), 10.69 (br, 1H), 12.67 (bs, 1H); $^{13}$C NMR (CD$_3$OD) d 51.1 (e), 106.3 (e), 113.1 (o), 113.5 (e), 120.4 (o), 127.4 (e), 129.2 (e) ×2, 130.8 (e), 150.8 (e), 164.7 (e); (DMSO-d$_6$) d 49.5, 103.9, 111.5, 112.2, 118.0, 126.2, 126.9, 127.3, 129.1, 148.8, 161.8; IR (nujol) 3158, 2356, 1685, 1625, 1190 cm$^{-1}$; UV (CH$_3$OH) 1$_{max}$ 270 (sh), 233, 209 nm; HRMS, calcd for C$_{11}$H$_{10}$N$_5$OBr$_2$ (MH$^+$) 385.9253, found 385.9250. 21.HCl: $^1$H NMR (CD$_3$OD) d 4.14 (s, 2H), 6.13 (s, 1H), 6.97 (s, 1H); $^{13}$C NMR (CD$_3$OD) d 50.7 (e), 107.2 (e), 112.2 (o), 115.3 (o), 118.4 (e), 125.6 (e), 127.3 (e), 127.6 (e), 127.7 (e), 148.6 (e), 164.3 (e). Anal. Calcd for C$_{11}$H$_9$N$_5$OBr$_2$.HCl: C, 31.20; H, 2.38; N, 16.54. Found: C, 31.39; H, 2.43; N, 16.40.

Stevensine (2). Method A: A solution of 19 (100 mg, 0.21 mmol) in 2 mL of methanesulfonic acid was heated in an unsealed flask at 90° C. for 12 h. After cooling, the reaction mixture was diluted with ether (10 mL×5), decanted, and the resulting residue was dissolved in MeOH (1 mL) and left standing overnight. The precipitate was filtered and washed with methanol (2×2 mL) to afford the methanesulfonic acid salt of 2 (62 mg, 61%) as a colorless solid. The free base of 2 was generated by passing the salt of 2 through a short plug of silica (CH$_2$Cl$_2$/MeOH sat. NH$_3$ 8:2). Method B: A solution of 16 (1.0 g, 2.4 mmol) and AI sulfate (0.38 g, 2.9 mmol) in 5 mL of methanesulfonic acid was heated at 90° C. for 20 h. Upon cooling, the reaction mixture was diluted with ether (50 mL×5), decanted, and the resulting residue was purified by flash chromatography (CH$_2$Cl$_2$/MeOH sat. with NH$_3$ 9:1) to afford 2 (0.28 g, 30%) as a colorless solid. $^1$H NMR (CD$_3$OD) d 3.50 (d, 2H, J=7.0), 6.06 (t, 1H, J=7.0), 6.42 (s, 1H); $^{13}$C NMR (CD$_3$OD) d 39.1, 100.0, 109.3, 116.6, 122.9, 125.3, 129.0, 130.4, 131.5, 150.9, 164.7; IR (nujol) 3158, 1625, 1415, 1190 cm$^{-1}$; UV (CH$_3$OH) 1$_{max}$ 274, 225 nm; HRMS, calcd for C$_{11}$H$_{10}$N$_5$OBr$_2$ (MH$^+$) 385.9253, found 385.9247. 2.CH$_3$SO$_3$H: $^1$H NMR (CD$_3$OD) d 2.70 (s, 3H), 3.58 (d, 2H, J =7.0), 6.26 (t, 1H, J=7.0), 6.82 (s, 1H); $^{13}$C NMR (CD$_3$OD) d 38.9, 39.5, 99.4, 109.6, 112.9, 123.4, 126.8, 127.1, 127.8, 129.3, 148.9, 164.2; UV (CH$_3$OH) 1$_{max}$ 284 (sh), 243 nm. Anal. Calcd for C$_{11}$H$_9$N$_5$OBr$_2$.CH$_3$SO$_3$H: C, 29.83; H, 2.71; N, 14.50. Found: C, 30.02; H, 2.79; N, 14.37.

(±)-4'-Bromohymenin (22). To a stirred solution of (±)-hymenin (1) (1.0 g, 2.6 mmol) in 20 mL of CF$_3$COOH was added Br$_2$ (0.16 mL, 3.1 mmol) at room temperature. After 20 min, the reaction mixture was concentrated under reduced pressure and the resulting residue was purified by flash chromatography (CH$_2$Cl$_2$/MeOH sat. with NH3 9:1) to afford 22 (1.1 g, 95%) as a colorless solid. $^1$H NMR (DMSO-d$_6$) d 1.99 (m, 2H), 3.12 (m, 2H), 4.03 (t, 1H, J=5.2), 5.05 (bs, 2H), 7.95 (brt, 1H), 10.23 (bs, 1H), 12.50 (br, 1H); IR (nujol) 3240, 2921, 1617, 1555 cm$^{-1}$; UV (CH$_3$OH) 1$_{max}$ 277, 213 nm; HRMS, calcd for C$_{11}$H$_{10}$N$_5$OBr$_3$ (M$^+$) 464.8436, found 464.8427. 22.HCl: $^1$H NMR (CD$_3$OD) d 2.21-2.13 (m, 2H), 2.33-2.24 (m, 2H), 3.35-3.25 (m 2H), 4.25 (dd, 1H, J=6.8, 5.5); $^{13}$C NMR (CD$_3$OD) d 34.3 (t), 36.5 (d), 39.6 (t), 96.2 (s), 102.4 (s), 108.6 (s), 124.7 (s), 126.1 (s), 127.4 (s), 148.9 (s), 164.0 (s). Anal. Calcd for C$_{11}$H$_{10}$N$_5$OBr$_3$.HCl: C, 26.19; H, 2.20; N, 13.88. Found: C, 26.11; H, 2.30; N, 13.87.

5-Bromostevensine (23). To a stirred solution of 1 (100 mg, 0.26 mmol) in 2 mL of methanesulfonic acid was added Br$_2$ (0.16 mL, 0.31 mmol) at room temperature. After 20 min, the reaction mixture was diluted with ether (10 mL×5), decanted, and the residue was purified by flash chromatography (CH$_2$Cl$_2$/MeOH sat. with NH3 9:1) to afford 23 (46 mg, 38%) as a colorless solid along with 22 (26 mg, 21%). $^1$H NMR (CD$_3$OD) d 4.12 (s, 2H), 6.92 (s, 1H); $^{13}$C NMR (CD$_3$OD) d 50.4, 99.9, 110.0, 116.0, 121.1, 124.3, 124.5, 125.8, 128.8, 148.6, 163.6; IR (nujol) 3146, 1684, 1548, 1406, 1185 cm$^{-1}$; UV (CH$_3$OH) 1$_{max}$ 286 (sh), 242; HRMS, calcd for C$_{11}$H$_8$N$_5$OBr$_3$ (M$^+$) 462.8280, found 462.8284.

Debromohymenialdisine (4) and 2,3-Debromostevensine (24). A solution of 22 (100 mg, 0.21 mmol) in 10 mL of 48% HBr was heated at 90° C. in a sealed tube for 4 h. The solvent was evaporated under reduced pressure and the resulting residue was purified by flash chromatography (CH$_2$Cl$_2$/MeOH sat. with NH3 8:2) to afford 24 (10 mg, 21%) as a colorless solid and 4 (20 mg, 40%) as a yellow solid. 24.HCl: $^1$H NMR (CD$_3$OD) d 3.61 (d, 2H, J=7.0), 6.13 (t, 1H, J=7.0), 6.40 (d 1H, J=2.8), 6.84 (s, 1H), 7.09 (d, 1H, J=2.8); $^{13}$C NMR (CD$_3$OD) d 39.3, 109.6, 112.7, 121.5, 123.7, 124.3, 127.0, 128.4, 129.6, 149.1, 166.1; UV (CH$_3$OH) 1$_{max}$ 265, 225 (sh) nm; HRMS, calcd for C$_{11}$H$_{12}$N$_5$O (MH$^+$) 230.1040, found 230.1035. Anal. Calcd for C$_{11}$H$_{11}$N$_5$O.HCl: C, 49.73; H, 4.55; N, 26.36. Found: C, 49.80; H, 4.50; N, 26.50. 4: $^1$H NMR (DMSO-d$_6$) d 3.18 (m, 2H), 3.34 (m, 2H), 6.95 (br, 1H), 6.97 (bs, 1H), 7.89 (bs, 1H), 7.91 (bs, 1H), 10.25 (br, 1H), 11.63 (bs, 1H); (CD$_3$OD) d 3.39 (m, 2H), 3.47 (m, 2H), 6.60 (br, 1H), 7.08 (d, 1H, J=2.8); IR (nujol) 3288, 2473, 1614, 1415, 1123 cm$^{-1}$; UV (CH$_3$OH) 1$_{max}$ 344, 268, 230 rim; HRMS, calcd for C$_{11}$H$_{12}$N$_5$O$_2$ (MH$^+$) 246.0991, found 246.0986. 4.HCl: $^1$H NMR (DMSO-d$_6$) d 3.30 (m, 4H), 6.60 (t, 1H, J=2.6), 7.10 (t, 1H, J=2.6), 8.08 (t, 1H, J=4.4), 8.80 (br, 1H), 9.20 (br, 1H), 11.30 (br, 1H), 12.14 (bs, 1H); (D$_2$O) d 3.34 (m, 2H), 3.40 (m, 2H), 6.58 (br, 1H, J=2.8), 7.15 (d, 1H, J=2.8); $^{13}$C NMR (DMSO-d$_6$) d 31.4, 39.2, 109.6, 119.6, 120.0, 122.8, 126.8, 130.2, 154.2, 162.9, 163.3; UV (CH$_3$OH) 1$_{max}$ 348, 250 (sh), 214 nm. Anal. Calcd for C$_{11}$H$_{11}$N$_5$O$_2$.HCl: C, 46.90; H, 4.29; N, 24.86. Found: C, 47.12; H, 4.37; N, 24.60.

3-Bromo-4,5'-dihydrohymenialdisine (25). A solution of 22 (100 mg, 0.21 mmol) in 10 mL of H$_2$O/acetic acid (1:1)

was refluxed for 12 h. The solvent was evaporated under reduced pressure and the resulting residue was purified by flash chromatography (CH$_2$Cl$_2$/MeOH saturated with NH$_3$ 8:2) to afford diastereomers 25a (32 mg, 38%) and 25b (29 mg, 34%) as colorless solids. 25a.HCl: $^1$H NMR (DMSO-d$_6$) d 1.50 (m, 1H), 1.97 (m, 1H), 3.12 (m, 2H), 3.49 (t, 1H, J=8.2), 4.85 (bs, 1H), 7.98 (bt, 1H), 8.88 (bs, 1H), 8.98 (bs, 1H), 9.64 (s, 1H), 12.45 (bs, 1H), 12.67 (s, 1H); $^{13}$C NMR (DMSO-d$_6$) d 28.0, 37.7, 37.8, 61.4, 99.3, 106.2, 121.9, 125.5, 158.9, 161.8, 173.3; IR (nujol) 3254, 3127, 1769, 1701, 1622, 1538, 1420, 1195, 1023, 984, 763 cm$^{-1}$; UV (CH$_3$OH) 1$_{max}$ 276, 229 (sh) nm; HRMS, calcd for C$_{11}$H$_{12}$N$_5$O$_2$Br$_2$ (MH$^+$) 403.9358, found 403.9360. 25b.HCl: $^1$H NMR (DMSO-d$_6$) d 1.80 (m, 1H), 2.08 (m, 1H), 3.10 (m, 2H), 3.52 (q, 1H, J=5.8), 4.59 (d, 1H, J=5.1), 7.89 (bt, 1H), 8.90 (bs, 1H), 9.22 (bs, 1H), 9.88 (s, 1H), 12.36 (bs, 1H), 12.60 (s, 1H); $^{13}$C NMR (DMSO-d$_6$) d 29.0, 37.5, 37.8, 60.8, 100.0, 105.7, 121.8, 125.5, 157.7, 161.7, 173.1; IR (nujol) 3264, 1769, 1705, 1626, 1538, 1408 cm$^{-1}$; UV (CH$_3$OH) 1$_{max}$ 276, 229 (sh) nm; HRMS, calcd for C$_{11}$H$_{12}$N$_5$O$_2$Br$_2$ (MH$^+$) 403.9358, found 403.9362.

Hymenialdisine (3). From 21: A solution of 21 (40 mg, 0.10 mmol) in 10 mL of H$_2$O/acetic acid (v/v 1:1) was refluxed for 2 d. The solvent was evaporated under reduced pressure and the resulting residue was purified by flash chromatography (CH$_2$Cl$_2$/MeOH sat. with NH3 8:2) to afford 3 (20 mg 65%) as a yellow solid. From 25: A solution of 25 (100 mg, 0.25 mmol) in 5 mL of methanesulfonic acid containing a catalytic amount of HBr (2 mL of a 10% HBr/CH$_3$SO$_3$H mixture) was heated at 90° C. in a stoppered flask for 12 h. The reaction mixture was diluted with ether (10 mL×5), decanted, and the residue was purified by flash chromatography (CH$_2$Cl$_2$/MeOH sat. with NH3 8:2) to afford 3 (27 mg, 33%) and 4 (17 mg, 27%) as yellow solids. Compound 3: $^1$H NMR (DMSO-d$_6$) d 3.18 (m, 2H), 3.30 (m, 2H), 7.10 (br, 2H), 7.28 (bs, 1H), 7.95 (bs, 1H), 10.25 (br, 1H), 12.28 (bs, 1H); 13C NMR (DMSO-d$_6$) d 29.6, 39.2, 103.8, 113.6, 122.5, 125.4, 126.8, 154.6, 162.5, 173.0; UV (CH$_3$OH) 1$_{max}$ 346, 270, 228 (sh) nm; HRMS calcd for C$_{11}$H$_{11}$N$_5$O$_2$Br (MH$^+$) 324.0097, found 324.0098. 3.HCl: $^1$H NMR (DMSO-d$_6$) d 3.25 (bs, 4H), 6.64 (s, 1H), 8.18 (bs, 1H), 8.88 (bs, 1H), 9.40 (bs, 1H), 11.20 (bs, 1H), 12.92 (bs, 1H); (D$_2$O) d 3.35 (m, 2H), 3.43 (m, 2H), 6.62 (s, 1H); $^{13}$C NMR (DMSO-d$_6$) d 31.8, 39.5, 105.2, 111.2, 120.5, 121.3, 128.3, 128.5, 154.5, 162.1, 163.0; IR (nujol) 3115, 1711, 1608, 1538, 1417, 1324 cm$^{-1}$; UV (CH$_3$OH) 1$_{max}$ 351, 260. Anal. Calcd for C$_{11}$H$_{10}$N$_5$O$_2$Br.HCl: C, 36.64; H, 3.07; N, 19.42. Found: C, 36.99; H, 3.16; N, 19.28.

3-Bromodebromohymenialdisine (26). To a stirred solution of 4 (20 mg, 0.08 mmol) in 5 mL of CF$_3$COOH was slowly added a solution of N-bromosuccinamide (15 mg, 0.08 mmol) in 5 mL of CF$_3$COOH at room temperature. After 30 min, the solvent was evaporated under reduced pressure and the residue was purified by flash chromatography, first, with EtOAc/acetone/H$_2$O/HCOOH 60:36:3.5:3.5 then again with CH$_2$Cl$_2$/MeOH sat. with NH$_3$ 8:2 to afford 26 (14 mg, 54%) as a colorless solid. $^1$H NMR (DMSO-d$_6$) d 3.20 (bs, 4H), 6.60 (br, 1H), 7.20 (s, 1H), 7.85 (bs, 2H), 8.66 (bs, 1H), 12.16 (bs, 1H); UV (CH$_3$OH) 1$_{max}$ 327, 268, 238 (sh) nm; HRMS, calcd for C$_{11}$H$_{11}$N$_5$O$_2$Br (MH$^+$) 324.0095, found 324.0089. 26.HCl: $^1$H NMR (DMSO-d$_6$) d 3.23 (bs, 4H), 7.28 (s, 1H), 8.02 (bs, 1H), 8.46 (br, 1H), 9.28 (br, 1H), 10.79 (br, 1H), 12.58 (bs, 1H); $^{13}$C NMR (DMSO-d$_6$) d 35.0 (e), 39.7 (e), 95.6 (e), 119.5 (e), 122.8 (e), 123.3 (o), 126.7 (e), 154.1 (e), 162.0 (e), 163.7 (e); IR (nujol) 3440, 1607, 1407, 1356, 1218 cm$^{-1}$; UV (CH$_3$OH) 1$_{max}$ 329, 260, 222 (sh) nm. Anal. Calcd for C$_{11}$H$_{10}$N$_5$O$_2$Br.HCl: C, 36.64; H, 3.07; N, 19.42. Found: C, 36.81; H, 3.16; N, 19.18.

References

1. For reviews of marine alkaloids, see: (a) Christophersen, C. in The Alkaloids: Chemistry and Pharmacology, Brossi, A., Ed.; Academic Press: N.Y., 1985; Vol. 24, pp 25–111. (b) Kobayashi, J. and Ishibashi, M. in The Alkaloids: Chemistry and Pharmacology, Brossi, A., Ed.; Academic Press: N.Y., 1992; Vol. 41, pp 41–124. (c) Faulkner, D. J. Nat. Prod. Rep., 1996, 13, 75, and earlier reports.

2. (a) Kobayashi, J.; Ohizumi Y.; Nakamura H.; Hirata, Y.; Wakamatsu, K.; Miyazawa, T. Experientia 1986, 42, 1064. (b) Kobayashi, J.; Nakamura, H.; Ohizumi, Y. Experientia 1988, 44, 86.

3. Albizati, K. F.; Faulkner, D. J. J. Org. Chem. 1985, 50, 4163.

4. Nanteuil, G. D.; Ahond, A.; Guilhem, J.; Poupat, C.; Dau, E. T. H.; Potier, P.; Pusset, M.; Pusset, J.; Laboute, P. Tetrahedron 1985, 41, 6019.

5. Cimino, G.; DeRosa, S.; DeStefano, S.; Mazzarella, L.; Puliti, R.; Sodano, G. Tetrahedron Lett. 1982, 23, 767.

6. Kitagawa, I.; Kobayashi, M.; Kitanaka, K.; Kido, M.; Kyogoku, Y. Chem. Pharm. Bull. 1983, 31, 2321.

7. Schmitz, F. J.; Gunasekera, S. P.; Lakshmi, V.; Tillekeratne, L. M. V. J. Nat. Prod. 1985, 48, 47.

8. Pettit, G. R.; Herald, C. L.; Leet, J. E.; Gupta, R.; Schaufelberger, D. E.; Bates, R. B.; Clewlow, P. J.; Doubek, D. L.; Manfredi, K. P.; Rutzler, K.; Schmidt, J. M.; Tackett, L. P.; Ward, F. B.; Bruck, M.; Camou, F. Can. J. Chem. 1990, 68, 1621.

9. Sharma, G. M.; Buyer, J. S.; Pomerantz, M. W. J. Chem. Soc. Chem. Commun. 1980, 435.

10. The closely related C$_{11}$N$_4$ metabolite axinohydantoin (ref. 8), isolated from Axinella sp. and Hymeniacidon sp. also possesses an a-monobromo pyrrole moiety.

11. The absolute configuration of hymenin (1), [a]$_D$-15° (MeOH) has not been determined.

12. Xu, Y.-z.; Phan, G.; Yakushijin, K.; Horne, D. A. Tetrahedron Lett. 1994, 35, 351.

13. (a) Remers, W. A. in Heterocyclic Compounds: Indoles Part I, Houlihan, W. J. Ed.: Wiley-Interscience, N.Y., 1972; pp 66–70. (b) Chadwick, D. J. in Comprehensive Heterocyclic Chemistry: The Structure, Reactions, Synthesis and Use of Heterocyclic Compounds, Katritzky, A. R. and Rees, C. W., Eds.; Pergamon, N.Y., 1984; Vol. 4; pp 206–209.

14. Bailey, D. M.; Johnson, R. E. J. Med. Chem. 1973, 16, 1300.

15. Gribble, G. W.; Switzer, F. L. Synth. Commun. 1987, 17, 377.

16. In the synthesis of (±)-hymenin (1), N-C coupling product analogous to 18 was also obtained in 17% yield from the reaction of olefin 13 and AI in CH$_3$SO$_3$H (23° C., 2 d) to afford 2,3-dibromo-4-(1H-imidazol-2-ylamino)-4,5,6,7-tetrahydro-1H-pyrrolo[2,3-c]azepin-8-one: $^1$H NMR (CD$_3$OD) d 1.92 (ddd, 1H, J=14.7, 10.2, 2.5), 2.42 (ddd, 1H, J=14.7, 7.2, 2.5), 3.22 (dd, 1H, J=14.8, 7.2), 3.55 (dd, 1H, J=14.8, 10.2), 4.88 (t, 1H, J=2.5), 6.55 (s, 2H); $^{13}$C NMR (CD$_3$OD) d 33.5 (t), 37.2 (t), 50.7 (d), 102.8 (s), 108.0 (s), 117.9 (d×2), 125.3 (s), 128.0 (s), 150.7 (s), 163.9 (s).

17. The N-C coupling product 18 was the predominant product after 1 d. This product is then transformed to the thermodynamically more stable isomer 19 after prolonged exposure to CH$_3$SO$_3$H for 7 d.

18. Ruasse, M.-F. Acc. Chem. Res. 1990, 23, 87.

19. 3-Debromostevensine (20) and 5-bromo-3-debromostevensine (21) were also obtained from the trans-bromination of 4'-bromohymenin (22). Xu, Y.-z.; Yakushijin, K.; Horne, D. A. Tetrahedron Lett. (in press).

20. March, J. in Advanced Organic Chemistry, 4th Ed,.; John Wiley and Sons: N.Y., 1992, p. 556.

21. (a) Ipso attack has been studied mostly for nitration, see March, J. in Advanced Organic Chemistry, 4th Ed.; John Wiley and Sons: N.Y., 1992, p. 458. (b) In the case of aluminum halide catalyzed isomerization of bromotoluenes, heating at 100° C. resulted in the formation of benzene, toluene, and xylenes. The formation of benzene and xylenes is probably due to ipso attack of Br$^+$, see Olah, G. A.; Meyer, M. W. J. Org. Chem., 1962, 27, 3464. (c) For bromination of aromatic compounds facilitated by strong acids, see Bull. Chem. Soc. Jpn. 1994, 67, 1918.

22. Prager, R. H.; Tsopelas, C. Aust. J. Chem. 1990, 43, 367.

23. Schimtz et al. (ref. 7) have reported sharp signals for the pyrrole hydrogens in the $^1$H NMR spectrum of debromohymenialdisine (4) in acidic media.

24. Anderson, H. J.; Lee, S. F. Can. J. Chem. 1956, 43, 409.

25. Baily, D. M.; Johnson, R. E.; Albertson, N. F. Org. Syn. 1971, 51, 100.

What is claimed is:

1. A compound having the structure:

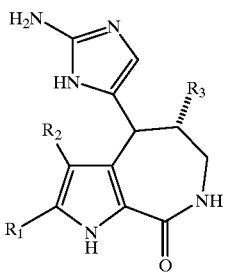

wherein R$_1$ and R$_2$ are the same or different and are H or a halogen and R$_3$ is a hydroxy group or a halogen.

2. The compound of claim 1, wherein R$_1$, R$_2$, and R$_3$ are Br.

3. A compound having the structure:

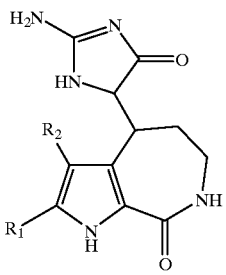

wherein R$_1$ and R$_2$ are the same or different and are H or a halogen.

4. The compound of claim 3, wherein R$_1$ and R$_2$ are Br.

5. A process for producing debromohymenialdisine, wherein the process comprises reacting the compound of claim 3 with CH$_3$SO$_3$H and catalytic HBr at about 90° C. in a sealed tube for about 12 hours.

6. The process of claim 5, wherein R$_1$ and R$_2$ are Br in the compound of claim 3.

7. A process for producing hymenialdisine, wherein the process comprises reacting the compound of claim 3 with CH$_3$SO$_3$H and catalytic HBr at about 90° C. in a sealed tube for about 12 hours.

8. The process of claim 7, wherein R$_1$ and R$_2$ are Br in the compound of claim 3.

9. A compound having the structure:

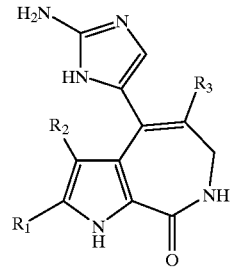

wherein R$_1$, R$_2$, and R$_3$ are Br.

10. A compound having the structure:

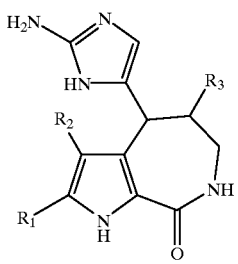

wherein each of R$_1$, R$_2$, and R$_3$ is H.

11. A process of producing a compound having the structure:

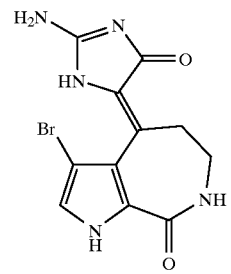

comprising reacting hymenin with Br$_2$ and HOAc under suitable conditions to produce the compound.

12. A process of converting hymenin to debromohymenialdisine, comprising a step of reacting hymenin with Br$_2$ under suitable conditions to form a precursor (compound 22) of debromohymenialdisine.

13. The process of claim 12, further comprising the step of reacting the (compound 22) precursor of debromohymenialdisine with HOAc/H$_2$O under suitable conditions to form debromohymenialdisine.

14. The process of claim 12, further comprising the step of reacting the (compound 22) precursor of debromohymenialdisine with aqueous HBr under suitable conditions to form debromohymenialdisine.

15. A process for producing debromohymenialdisine, wherein the process comprises reacting a compound having the structure:

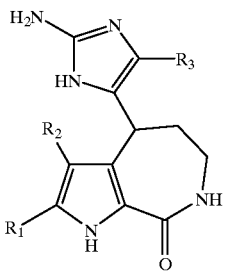

wherein $R_1$ and $R_2$ are the same or different and are H or a halogen, and $R_3$ is a halogen,
with aqueous HBr at about 90° in a sealed tube.

16. The process of claim 15, wherein $R_1$, $R_2$, and $R_3$ are Br.

17. The process of claim 5, wherein the compound of claim 11 is produced by a second process comprising reacting a compound having the structure:

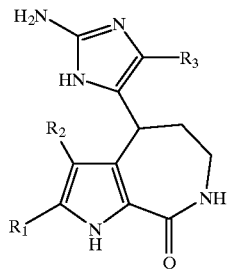

wherein $R_1$ and $R_2$ are the same or different and are H or a halogen, and $R_3$ is a halogen, with acetic acid and water by reflux.

18. The process of claim 6, wherein the compound of claim 11 is produced by a second process comprising reacting a compound having the structure:

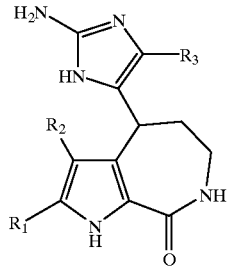

wherein $R_1$ and $R_2$ are the same or different and are H or a halogen, and $R_3$ is a halogen, with acetic acid and water by reflux.

19. The process of claim 7, wherein the compound of claim 11 is produced by a second process comprising reacting a compound having the structure:

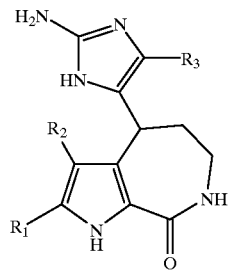

wherein $R_1$ and $R_2$ are the same or different and are H or a halogen, and $R_3$ is a halogen, with acetic acid and water by reflux.

20. The process of claim 8, wherein the compound of claim 3 is produced by a second process comprising reacting a compound having the structure:

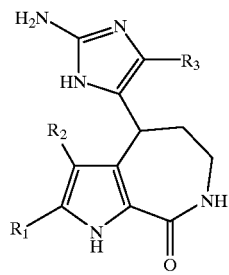

wherein $R_1$ and $R_2$ are the same or different and are H or a halogen, and $R_3$ is a halogen, with acetic acid and water by reflux.

21. A process for producing hymenialdisine, wherein the compound having the structure:

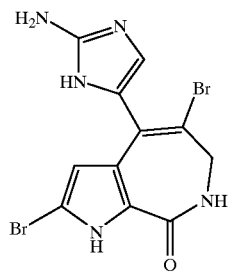

is reacted with $CH_3SO_3H$ and catalytic HBr at about 90° in a sealed tube for about 12 hours.

* * * * *